(12) United States Patent
Yasuhara et al.

(10) Patent No.: US 7,381,746 B2
(45) Date of Patent: Jun. 3, 2008

(54) 2-AMINOBICYCLO[3.1.0]HEXANE-2,6-DICARBOXYLIC ACID DERIVATIVE

(75) Inventors: Akito Yasuhara, Tokyo (JP); Kazunari Sakagami, Tokyo (JP); Hiroshi Ohta, Tokyo (JP); Atsuro Nakazato, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 73 days.

(21) Appl. No.: 10/562,010

(22) PCT Filed: Jun. 25, 2004

(86) PCT No.: PCT/JP2004/009384

§ 371 (c)(1),
(2), (4) Date: Dec. 23, 2005

(87) PCT Pub. No.: WO2005/000790

PCT Pub. Date: Jan. 6, 2005

(65) Prior Publication Data

US 2006/0142388 A1   Jun. 29, 2006

(30) Foreign Application Priority Data

Jun. 26, 2003   (JP)   ............ 2003-181931

(51) Int. Cl.
*A01N 37/12* (2006.01)
(52) U.S. Cl. ................................... 514/561
(58) Field of Classification Search ............ None
See application file for complete search history.

(56) References Cited

U.S. PATENT DOCUMENTS

| | | | |
|---|---|---|---|
| 5,912,248 A * | 6/1999 | Fernandez et al. | 514/256 |
| 5,916,920 A * | 6/1999 | Fernandez et al. | 514/561 |
| 6,479,674 B1 * | 11/2002 | Nakazato et al. | 549/426 |
| 6,500,958 B2 * | 12/2002 | Nakazato et al. | 548/301.1 |
| 6,770,676 B2 * | 8/2004 | Nakazato et al. | 514/561 |
| 7,034,055 B1 * | 4/2006 | Curry | 514/567 |

FOREIGN PATENT DOCUMENTS

| | | |
|---|---|---|
| JP | 2000-500754 A | 1/2000 |
| JP | 2000-86597 A | 3/2000 |
| JP | 2000-336071 A | 12/2000 |
| JP | 2001-525825 A | 12/2001 |
| WO | WO 02/68380 A1 | 9/2002 |

OTHER PUBLICATIONS

Silverman. The Organic Chemistry of Drug Design and Drug Action.Academic Press:1992,pp. 15-22.*

* cited by examiner

*Primary Examiner*—Yvonne Eyler
*Assistant Examiner*—MLouisa Lao
(74) *Attorney, Agent, or Firm*—Sughrue Mion, PLLC

(57) ABSTRACT

One object of the present invention is to provide a drug that is effective in treatments for and prevention of psychiatric disorders and in treatments for and prevention of neurological diseases, inhibiting a Group II metabotropic glutamate receptor.

The object is solved by a 2-amino-bicyclo[3.1.0]hexane-2, 6-dicarboxylic acid derivative represented by formula [I]:

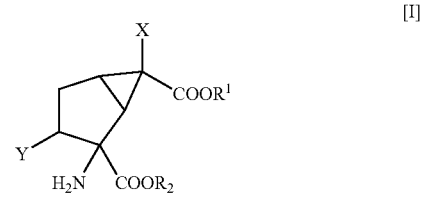

(wherein $R^1$ and $R^2$ are the same or different, and each represents a hydrogen atom, $C_{1-10}$alkyl group, etc; X represents a hydrogen atom or a fluorine atom; and Y represents an amino group, $-SR^3$, $-S(O)_nR^7$, $-SCHR^3R^4$, $-S(O)_nCHR^3R^4$, $-NHCHR^3R^4$, $-N(CHR^3R^4)(CHR^5R^6)$, $-NHCOR^3$ or $-OCOR^7$), a pharmaceutically acceptable salt thereof, or a hydrate thereof and so on.

10 Claims, No Drawings

2-AMINOBICYCLO[3.1.0]HEXANE-2,6-DICARBOXYLIC ACID DERIVATIVE

This is a U.S. national stage of Application No. PCT/JP2004/009384 filed Jun. 25, 2004.

FIELD OF THE INVENTION

The present invention relates to pharmaceutically effective 2-amino-bicyclo[3.1.0]hexane-2,6-dicarboxylic acid derivative, a pharmaceutically acceptable salt thereof and a hydrates thereof, and drug containing them as an active ingredient. More specifically, the present invention relates to a novel 2-amino-bicyclo[3.1.0]hexane-2,6-dicarboxylic acid derivative effective for the treatments and preventions of psychiatric disorders such as schizophrenia, anxiety and related ailments, bipolar disorder and epilepsy, and those of neurological diseases such as drug dependence, cognitive disorder, Alzheimer's disease, Huntington's chorea, Parkinson's disease, dyskinesia associated with muscular rigidity, cerebral ischaemia, cerebral failure, myelopathy and head trauma.

BACKGROUND OF THE INVENTION

In recent years, successive clonings of glutamate receptor genes have revealed that glutamate receptors have a surprisingly large number of subtypes. At present, glutamate receptors are classified into two major groups: an "ionotropic type in which the receptor has a ion channel type structure" and a "metabotropic type in which the receptor is coupled with G-protein" (see Science, 258, p. 597-603, 1992 (Non-Patent Document 1 mentioned below)). The ionotropic glutamate receptors are classified pharmacologically into three subgroups: N-methyl-D-asparaginic acid (NMDA); α-amino-3-hydroxy-5-methylisoxazole-4-propionate (AMPA); and kainate (see Non-Patent Document 1). The metabotropic glutamate receptors are classified into eight sub-groups from type 1 to type 8 (see J. Neurosci., 13, p. 1372-1378, 1993 (Non-Patent Document 2 mentioned below), and Neuropharmacol., 34, p. 1-26, 1995 (Non-Patent Document 3 mentioned below)).

The metabotropic glutamate receptors are classified pharmacologically into three groups. Of these, the Group II receptors (mGluR2/mGluR3) bind with adenylcyclase, and inhibit the Forskolin stimulated accumulation of cyclic adenosine monophosphate (cAMP) (see Trends Pharmacol. Sci., 14, 13, 1993 (Non-Patent Document 4 mentioned below)). Thus, it is suggested that compounds, which antagonize the action of Group II metabotropic glutamate receptors, will be effective for the treatment and prevention of acute and chronic psychiatric disorders and neurological diseases.

LIST OF RELATED DOCUMENTS

| | |
|---|---|
| Non-Patent Document 1: | Science, 258, p. 597-603, 1992 |
| Non-Patent Document 2: | J. Neurosci., 13, p. 1372-1378, 1993 |
| Non-Patent Document 3: | Neuropharmacol., 34, p. 1-26, 1995 |
| Non-Patent Document 4: | Trends Pharmacol. Sci., 14, p. 13, 1993 |

The object of the present invention is to provide a drug that antagonizes the action of Group II metabotropic glutamate receptors, and would be effective for the treatment and prevention of psychiatric disorders such as schizophrenia, anxiety and related ailments thereof, depression, bipolar disorder and epilepsy, and also effective for the treatment and prevention of neurological diseases such as drug dependence, cognitive disorder, Alzheimer's disease, Huntington's chorea, Parkinson's disease, dyskinesia associated with muscular rigidity, cerebral ischaemia, cerebral failure, myelopathy and head trauma.

DISCLOSURE OF THE INVENTION

The present inventors have conducted extensive examinations into pharmacological effects of 2-amino-bicyclo[3.1.0]hexane-2,6-dicarboxylic acid derivatives, and discovered novel 2-amino-bicyclo[3.1.0]hexane-2,6-dicarboxylic acid derivatives and esters of the derivatives affect of activity of Group II metabotropic glutamate receptors, thereby completing the present invention.

The compound of the present invention is a 2-amino-bicyclo[3.1.0]hexane-2,6-dicarboxylic acid derivative, (hereafter referred as 'the compound of the present invention')' represented by formula [I] and a pharmaceutically acceptable salt and or a hydrate of the derivative.

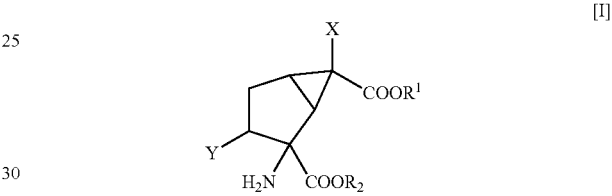

[wherein $R^1$ and $R^2$ are the same or different, and each represents, a hydrogen atom, a $C_{1-10}$ alkyl group, a phenyl group, a naphthyl group, a $C_{1-10}$ alkyl group substituted by one or two phenyl groups, a $C_{2-10}$ alkenyl group, a $C_{2-10}$ alkynyl group, a hydroxyl $C_{2-10}$ alkyl group, a $C_{1-10}$ alkoxycarbonyl $C_{1-10}$ alkyl group, an amino $C_{2-10}$ alkyl group or a $C_{1-10}$ alkoxy $C_{1-10}$ alkyl group;

X represents a hydrogen atom or a fluorine atom;

Y represents an amino group, $-SR^3$, $-S(O)_nR^7$, $-SCHR^3R^4$, $-S(O)_nCHR^3R^4$, $-NHCHR^3R^4$, $-N(CHR^3R^4)(CHR^5R^6)$, $-NHCOR^3$ or $-OCOR^7$ (wherein $R^3$, $R^4$, $R^5$ and $R^6$ are the same or different, and each represents a hydrogen atom, a $C_{1-10}$ alkyl group, a phenyl group, a naphthyl group, a naphthyl group substituted by one to seven halogen atoms, a hetroaromatic group or else represents "a phenyl group substituted by one to five substituents selected from a group consisting of a halogen atom, a phenyl group, a $C_{1-10}$ alkyl group, a $C_{1-10}$ alkoxy group and a trifluoromethyl group";

$R^7$ represents a $C_{1-10}$ alkyl group, a phenyl group, a naphthyl group, a naphthyl group substituted by one to seven halogen atoms, a hetroaromatic group or else represents "a phenyl group substituted by one to five substituents selected from a group consisting of a halogen atom, a phenyl group, a $C_{1-10}$ alkyl group, a $C_{1-10}$ alkoxy group and a trifluoromethyl group", and n represents an integer 1 or 2]

The terms used in the present specification are defined as follows.

The $C_{1-10}$ alkyl group means a straight-chain alkyl group having one to ten carbon atoms, a branched chain alkyl group having three to ten carbon atoms or a cyclic alkyl group having three to ten carbon atoms. Examples of the straight-chain alkyl group include a methyl group, an ethyl group, a propyl group, a butyl group, a pentyl group, a hexyl group, a heptyl group, an octyl group, a nonyl group and a decyl group. Examples of the branched chain alkyl group include an isopropyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 5-methylhexyl group, a 3-ethylpentyl group, a 1-propylbutyl group, a 1,4-dimethylpentyl group, a 3,4-dimethylpentyl group, a 1,2,3-trimethylbutyl group, a 1-isopropylbutyl group, a 4,4-dimethylpentyl group, a 5-methylheptyl group, a 4-ethylhexyl group, a 2-propylpentyl group, a 2,5-dimethylhexyl group, a 4,5-dimethylhexyl group, a 2-ethyl-3-methylpentyl group, a 1,2,4-trimethylpentyl group, a 2-methyl-1-isopropylbutyl group, a 3-methyloctyl group, a 2,5-dimethylheptyl group, a 1-(1-methylpropyl)-2-methylbutyl group, a 1,4,5-trimethylhexyl group, a 1,2,3,4-tetramethylpentyl group, a 6-methylnonyl group, a 5-ethyl-2-methylheptyl group, a 2,3-dimethyl-1-(1-methylpropyl) butyl group, a cyclopropylmethyl group, a 2-(cyclopropyl) ethyl group, a 3-(cyclobutyl)pentyl group, a cyclopentylmethyl group and a cyclohexylmethyl group Examples of the cyclic alkyl group include a cyclopropyl group, a cyclobutyl group, a cyclopentyl group, a cyclohexyl group, a cycloheptyl group and a cyclooctyl group.

The $C_{2-10}$ alkenyl group means a straight-chain alkenyl group with at least one double bond having two to ten carbon atoms, a branched chain alkenyl group with at least one double bond having three to ten carbon atoms or a cyclic alkenyl group with at least one double bond having five to ten carbon atoms, examples of which include a vinyl group, an allyl group, a 3-butenyl group, a 4-pentenyl group, a 5-hexenyl group, a 6-heptenyl group, a 7-octenyl group, a 8-noneyl group, a 9-decenyl group, a 1-methyl-2-butenyl group, a 2-methyl-2-butenyl group, a 2-methyl-3-butenyl group, a 2-pentenyl group, a 2-methyl-2-hexenyl group and a 2-cyclopentenyl group.

The $C_{2-10}$ alkynyl group means a straight-chain alkynyl group with at least one triple bond having two to ten carbon atoms or a branched chain alkynyl group with at least one triple bond having four to ten carbon atoms, examples of which include a 2-propynyl group, a 3-butynyl group, a 4-pentynyl group, a 5-hexynyl group, a 6-heptynyl group, a 7-octynyl group, a 8-nonyl group, a 9-decinyl group, a 3-pentynyl group and a 4-methyl-2-pentynyl group.

The $C_{1-10}$ alkyl group substituted by one or two phenyl groups means, for example, a benzyl group, a diphenylmethyl group, a 2-phenylethyl group, a 2-phenylpropyl group, a 1-methyl-1-phenylethyl group or a 1-methyl-2-phenylpentyl group.

The hydroxy $C_{2-10}$ alkyl group means a $C_{2-10}$ alkyl group substituted by at least one hydroxyl group, examples of which include a 2-hydroxyethyl group, a 3-hydroxypropyl group, a 4-hydroxybutyl group, a 5-hydroxypentyl group, a 6-hydroxyhexyl group, a 7-hydroxyheptyl group, a 8-hydroxyoctyl group, a 9-hydroxynonyl group, a 10-hydroxydecyl group, a 2-hydroxypropyl group, a 2,3-dihydroxypropyl group and a 2-hydroxy-3-methylbutyl group.

The $C_{1-10}$ alkoxycarbonyl $C_{1-10}$ alkyl group means a alkyl group having one to ten carbons which is substituted by a straight-chain or branched chain alkoxycarbonyl group having one to six carbons, examples of which include a methoxycarbonylmethyl group, an ethoxycarbonylmethyl group, a propyloxycarbonylmethyl group, an isopropoxycarbonylmethyl group, a butyltoxycarbonylmethyl group, an isobutoxycarbonylmethyl group, a t-butoxycarbonylmethyl group, a pentyloxycarbonylmethyl group, a hexyloxycarbonylmethyl group, a 2-(ethoxycarbonyl)ethyl group, a 3-(ethoxycarbonyl)propyl group, a 4-(ethoxycarbonyl)butyl group, a 4-(ethoxycarbonyl)pentyl group and a 4-(ethoxycarbonyl)-3-methylpentyl group.

The amino $C_{2-10}$ alkyl group means a $C_{2-6}$ alkoxy group substituted by at least one amino group, examples of which include a 2-aminoethyl group, a 3-aminopropyl group, a 4-aminobutyl group, a 5-aminobutyl group, a 7-aminoheptyl group, a 2-aminopropyl group and a 2,4-diaminobutyl group.

The $C_{1-10}$ alkoxy $C_{1-10}$ alkyl group means a alkyl group having one to ten carbons which is substituted by a straight-chain or branched chain alkoxy group having one to ten carbons, examples of which include a 2-methoxyethyl group, a 2-ethoxyethyl group, a 2-propoxyethyl group, a 2-isopropoxyethyl group, a 2-butoxyethyl group, a 2-isobutoxyethyl group, a 2-t-butoxyethyl group, a 2-pentyloxyethyl group, a 2-hexenyloxyethyl group, a 3-ethoxypropyl group, a 4-ethoxybutyl group, a 4-ethoxy-3-methoxybutyl group and a 4-ethoxy-3-methylpentyl group.

The naphthyl group substituted by one to seven halogen atoms means a naphthyl group substituted by at least one fluorine atom, chloride atom, bromine atom or iodine atom, examples of which include a 1-fluoro-2-naphthyl group, a 2-fluoro-1-naphthyl group, a 1-chloro-2-naphthyl group, a 2-chloro-1-naphthyl group, a 1-bromo-2-naphthyl group, a 2-bromo-1-naphthyl group, a 1-iodo-2-naphthyl group, a 2-iodo-1-naphthyl group, and a 1,3-difluoro-2-naphthyl group.

The hetroaromatic group means a monocyclic aromatic 5 membered or 6 membered ring containing at least an oxygen atom, a nitrogen atom or a sulfur atom; a monocyclic ring such as above which is fused with a benzene ring; or a hetrocyclic aromatic ring which is fused with one another. Examples of the hetroaromatic group include furyl, pyrrolyl, thiophenyl, oxazoyl, isoxazoyl, imidazoyl, pyrazoyl, thiazoyl, isothiazoyl, oxadiazoyl, thiadiazoyl, benzofuranyl, indolyl, benzothiophenyl, indazoyl, benzoisoxazoyl, benzoisothiazoyl, benzoimidazoyl, benzooxazoyl, benzothiazoyl, pyrizinyl, quinolinyl, isoquinolinyl, pyrodazinyl, pyrimizinyl, pyradinyl, cinnolinyl, phthalazinyl, quinazolinyl and quinoxalinyl.

The "phenyl group substituted by one to five substituents selected from a group containing a halogen atom, a phenyl group, a $C_{1-10}$ alkyl group, a $C_{1-10}$ alkoxy group and a trifluoromethyl group" means a phenyl group substituted by one to five substituents selected from a fluorine atom, a chloride atom, a bromine atom, an iodine atom, a phenyl group, a $C_{1-10}$ alkyl group, a $C_{1-10}$ alkoxy group and a trifluoromethyl group, examples of which include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-phenylphenyl group, a 3-phenylphenyl group, a 4-phenylphenyl group, a 2-methylphenyl group, a 3-methylphenyl group, a 4-methylphenyl group, a 2-ethylphenyl group, a 3-ethylphenyl group, a 4-ethylphenyl group, a 2-(1-propyl)phenyl group, a 3-(1-propyl)phenyl group, a 4-(1-propyl)phenyl group, a 2-isopropylphenyl group, a 3-isopropylphenyl group, a 4-isopropylphenyl group, a 2-t-butylphenyl group, a 3-t-butylphenyl group, a 4-t-butylphenyl group, a 2-cyclopropylphenyl group, a 3-cyclopropylphenyl group, a 4-cyclopropylphenyl group, a 2-cyclohexylphenyl group, a 3-cyclohexylphenyl group, a 4-cyclohexylphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-(1-peropyloxy)phenyl group, a 3-(1-peropyloxy)phenyl group a 4-(1-peropyloxy)phenyl group, a 2-isopropoxyphenyl group, a 3-isopropoxyphenyl group a 4-isopropoxyphenyl group, a 2-cyclobutyloxyphenyl group, a 3-cyclobutyloxyphenyl group, a 4-cyclobutyloxyphenyl group, a 2-cyclohexyloxyphenyl group, a 3-cyclohexyloxyphenyl group, a 4-cyclohexyloxyphenyl group, a 2-trifluoromethylphenyl group, a 3-fluoromethylphenyl group, a 4-trifluoromethylphenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2,3-dibromophenyl group, a 2,4-dibromophenyl group, a 2,5-dibromophenyl group, a 2,6-dibromophenyl group, a 3,4-dibromophenyl group, a 3,5-dibromophenyl group, a 2,3-diiodophenyl group, a 2,4-diiodophenyl group, a 2,5-diiodophenyl group, a 2,6-diiodophenyl group, a 3,4-diiodophenyl group, a 3,5-diiodophenyl group, a 2,3-dicyanophenyl group, a 2,4-dicyanophenyl group, a 2,5-dicyanophenyl group, a 2,6-dicyanophenyl group, a 3,4-dicyanophenyl group, a 3,5-dicyanophenyl group, a 2,3-diphenylphenyl group, a 2,4-diphenylphenyl group, a 2,5-diphenylphenyl group, a 2,6-diphenylphenyl group, a 3,4-diphenylphenyl group, a 3,5-diphenylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,3-diisopropylphenyl group, a 2,4-diisopropylphenyl group, a 2,5-diisopropylphenyl group, a 2,6-diisopropylphenyl group, a 3,4-diisopropylphenyl group, a 3,5-diisopropylphenyl group, a 2,3-di(t-butyl)phenyl group, a 2,4-di(t-butyl)phenyl group, a 2,5-di(t-butyl)phenyl group, a 2,6-di(t-butyl)phenyl group, a 3,4-di(t-butyl)phenyl group, a 3,5-di(t-butyl)phenyl group, a 2,3-dicyclohexylphenyl group, a 2,4-dicyclohexylphenyl group, a 2,5-dicyclohexylphenyl group, a 2,6-dicyclohexylphenyl group, a 3,4-dicyclohexylphenyl group, a 3,5-dicyclohexylphenyl group, a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 2,3-ditrifluoromethylphenyl group, a 2,4-ditrifluoromethylphenyl group, a 2,5-ditrifluoromethylphenyl group, a 2,6-ditrifluoromethylphenyl group, a 3,4-ditrifluoromethylphenyl group, a 3,5-ditrifluoromethylphenyl group, a 2-chloro-3-fluorophenyl group, a 2-chloro-4-fluorophenyl group, a 2-chloro-5-fluorophenyl group, a 2-chloro-6-fluorophenyl group, a 3-chloro-4-fluorophenyl group, a 3-chloro-6-fluorophenyl group, a 5-chloro-2-fluorophenyl group, a 4-chloro-3-fluorophenyl group, a 4-chloro-2-fluorophenyl group, a 3-chloro-2-fluorophenyl group, a 3-bromo-2-chlorophenyl group, a 4-bromo-2-chlorophenyl group, a S-bromo-2-chlorophenyl group, a 2-bromo-6-chlorophenyl group, a 4-bromo-3-chlorophenyl group, a 3-bromo-5-iodophenyl group, a 4-bromo-2-iodophenyl group, a 4-bromo-3-iodophenyl group, a 3-bromo-2-iodophenyl group, a 2-chloro-3-methylphenyl group, a 2-chloro-4-methylphenyl group, a 2-chloro-5-methylphenyl group, a 2-chloro-6-methylphenyl group, a 3-chloro-4-methylphenyl group, a 3-fluoro-5-methoxyphenyl group, a 5-fluoro-2-methoxyphenyl group, a 4-fluoro-2-methoxyphenyl group, a 3-fluoro-2-methoxyphenyl group, a 2-fluoro-3-trifluoromethylphenyl group, a 2-fluoro-4-trifluoromethylphenyl group, a 2-fluoro-5-trifluoromethylphenyl group, a 2-fluoro-6-trifluoromethylphenyl group, a 3-fluoro-4-trifluoromethylphenyl group, a 2,3,4-trichlorophenyl group, a 2,3,5-trichlorophenyl group, a 2,4,5-trichlorophenyl group, a 2,4,6-trichlorophenyl group, a 3,4,5-trichlorophenyl group, a 2,3,4-tribromophenyl group, a 2,3,5-tribromophenyl group, a 2,4,5-tribromophenyl group, a 2,4,6-tribromophenyl group, a 3,4,5-tribromophenyl group, a 2,3,4-trifluorophenyl group, a 2,3,5-trifluorophenyl group, a 2,4,5-fluorophenyl group, a 2,4,6-trifluorophenyl group, a 3,4,5-trifluorophenyl group, a 2,3,4-triiodophenyl group, a 2,3,5-triiodophenyl group, a 2,4,5-triiodophenyl group, a 2,4,6-triiodophenyl group, a 3,4,5-triiodophenyl group, a 2,3,4-triphenylphenyl group, a 2,3,5-triphenylphenyl group, a 2,4,5-triphenylphenyl group, a 2,4,6-triphenylphenyl group, a 3,4,5-triphenylphenyl group, a 2,3,4-trimethylphenyl group, a 2,3,5-trimethylphenyl group, a 2,4,5-trimethylphenyl group, a 2,4,6-trimethylphenyl group, a 3,4,5-trimethylphenyl group, a 2,3,4-triethylphenyl group, a 2,3,5-triethylphenyl group, a 2,4,5-triethylphenyl group, a 2,4,6-triethylphenyl group, a 3,4,5-triethylphenyl group, a 2,3,4-triisopropylphenyl group, a 2,3,5-triisopropylphenyl group, a 2,4,5-triisopropylphenyl group, a 2,4,6-triisopropylphenyl group, a 3,4,5-triisopropylphenyl group, a 2,3,4-tri(t-butyl)phenyl group, a 2,3,5-tri(t-butyl)phenyl group, a 2,4,5-tri(t-butyl)phenyl group, a 2,4,6-tri(t-butyl)phenyl group, a 3,4,5-tri(t-butyl)phenyl group, a 2,3,4-trimethoxyphenyl group, a 2,3,5-trimethoxyphenyl group, a 2,4,5-trimethoxyphenyl group, a 2,4,6-trimethoxyphenyl group, a 3,4,5-trimethoxyphenyl group, a 2,3,4-tri(trifluoromethyl)phenyl group, a 2,3,5-tri(trifluoromethyl)phenyl group, a 2,4,5-tri(trifluoromethyl)phenyl group, a 2,4,6-tri(trifluoromethyl)phenyl group, a 3,4,5-tri(trifluoromethyl)phenyl group, a 4-chloro-2,3-difluorophenyl group, a 5-chloro-2,3-difluorophenyl group, a 2-chloro-5,6-difluorophenyl group, a 4-chloro-2,5-difluorophenyl group, a 4-chloro-5,6-difluorophenyl group, a 2-chloro-4,6-difluorophenyl group, a 4-chloro-2,6-difluorophenyl group, a 3-chloro-2,6-difluorophenyl group, a 2-chloro-3,6-difluorophenyl group, a 2-chloro-3,4-difluorophenyl group, a 2-chloro-4,5-difluorophenyl group, a 2-chloro-3,5-difluorophenyl group, a 2,3-dichloro-5,6-difluorophenyl group, a 4,5-dichloro-2,3-difluorophenyl group, a 4,6-dichloro-2,3-difluorophenyl group, a 3,5-dichloro-2,4-difluorophenyl group, a 2,3-dichloro-4,6-difluorophenyl group, a 3,6-dichloro-2,4-difluorophenyl group, a 2,3-dichloro-5,6-dimethylphenyl group, a 4,5-dichloro-2,3-dimethylphenyl group, a 4,6-dichloro-2,3-dimethylphenyl group, a 3,5-dichloro-2,4-dimethylphenyl group, a 2,3-dichloro-4,6-dimethylphenyl group, a 3,6-dichloro-2,4-dimethylphenyl group and a 2,3,4,5,6-pentafluorophenyl group.

The pharmaceutically acceptable salt of the present invention means, for example, a salt with a mineral acid such as sulfuric acid, hydrochloric acid or phosphoric acid, a salt with an organic acid such as acetic acid, oxalic acid, lactic acid, tartaric acid, fumaric acid, maleic acid, methanesulfonic acid or benzenesulfonic acid, a salt with an amine such as trimethylamine or methylamine, or a salt with a metal ion such as sodium ion, potassium ion or calcium ion.

The hydrate of the present invention means pharmaceutically acceptable hydrates of the compound of the present invention or their salts. The compound of the present invention and their salts may absorb moisture, accumulate drops of water, or become a hydrate by being exposed to the atmosphere or by recrystallization. The hydrate used in the present invention includes such a hydrate.

In the compounds represented by formula [I], there are five asymmetric carbon atoms are present in the bicyclo [3.1.0]hexane ring.

The compounds of the present invention are optically active bodies, and have stereo structure a represented by formula [II] below, its enantiomers or enantiomer mixtures such as racemic bodies. The compounds of the present invention include all of these optically active compounds represented by formula [II], the enantiomer mixtures such as racemic bodies, and the diastereomer mixtures.

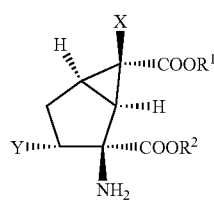

[II]

Notably the derivatives of the present compound in which either one or both of $R^1$ and $R^2$ in formula [I] or [II] are other than a hydrogen atom, in other words ester derivatives has no effect on Group II metabotropic glutamate receptors. However, this ester derivatives are hydrolyzed in vivo and converted into 2-amino-bicyclo[3.1.0]hexane-2,6-dicarboxylic acid derivatives which have a strong antagonistic effect on Group II metabotropic receptors. Therefore, these ester derivatives may be extremely effective compounds useful as prodrugs.

BEST METHOD FOR CARRYING OUT THE INVENTION

The present invention relates to a compound of the present invention represented by formula [I], a pharmaceutically acceptable salt thereof and a hydrate thereof. Compounds of the present invention represented by formula [I] may be synthesized by means of publicly known methods of organic synthesis, and may be prepared, for example, according to the preparation methods below. Also, synthetic intermediate (6), which is required to synthesize the compounds of the present invention represented by formula [I], may be prepared according to the following method. (In the formulas below, X, Y, n, and $R^1$ to $R^7$ are the same as described above. $R^8$ represents an aryl group or alkylsulfonyl group such as a mesyl group, a phenylsulfonyl group, a tosyl group or a trifluoromethylsulfonyl group; a benzoyl group; or a 4-nitrobenzoyl group. $R^9$ represents a protecting group for an amino group, examples of which include an alkoxycarbonyl group such as a methoxycarbonyl group, an ethoxycarbonyl group, a t-butoxycarbonyl group or a benzyloxycarbonyl group; an acyl group such as a benzoyl group, a p-phenylbenzoyl group or a (pyridine-2-yl) carbonyl group; an alkyl group such as an allyl group, a benzyl group, a p-methoxybenzyl group or a di(p-methoxyphenyl)methyl group; an alkenyl group such as a 5,5-dimethyl-3-oxo-1-cyclohexenyl group; a sulfenyl group such as a benzenesulfenyl group or a 2,4-dinitrosulfenyl group; a benzylsulfonyl group; a diphenylphosphinyl group; or an alkylphosphoryl group. $A^1$ represents —$R^3$ or —$CHR^3R^4$. $A^2$ represents —$R^5$ or —$CHR^3R^4$. Q represents —$SR^3$, —$S(O)_nR^7$, —$SCHR^3R^4$ or —$S(O)_nCHR^3R^4$).

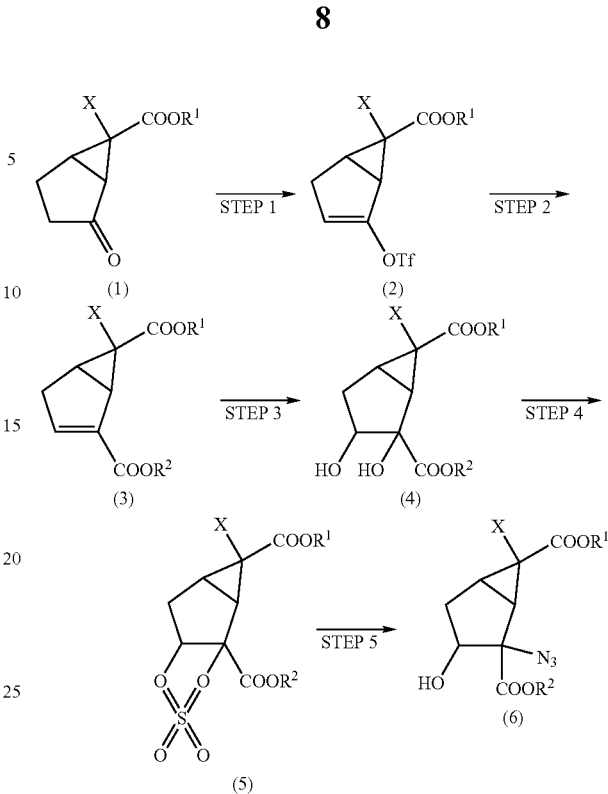

Step 1: Compound (2) may be prepared, for example, by reacting compound (1) with a trifluoromethanesulfonylating agent such as trifluoromethanesulfonic acid anhydride or N-phenyl-bis(trifluoromethanesulfonimide), in an inert solvent, in the presence of a base. Compound (1) may be prepared, for example, by means of the method described in "J. Med. Chem. 40, pp. 528-537, (1997)". Examples of the inert solvent include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; or a mixture of these solvents. Examples of the base include amines such as triethylamine, N-methylmorpholine, diisopropylethylamine and pyridine; inorganic bases such as potassium hydride and sodium hydride; metal amides such as lithium diisopropylamide, potassium bis(trimethylsilyl)amide and lithium bis(trimethylsilyl)azide; and metal alcoholates such as sodium, methoxide and potassium t-butoxide. The reaction temperature of Step 1 is, for example, −78° C. to room temperature. A preferred example of Step (1) is to synthesize compound (2) by reacting compound (1) with N-phenyl-bis(trifluoromethanesulfonimide), in a solvent of tetrahydrofuran, in the presence of lithium hexamethyldisilazane.

Step 2: Compound (3) may be prepared, for example, by reacting compound (2) with carbon monoxide and $R^2OH$, in the presence of organic bases such as triethylamine, N-methylmorpholine, diisopropylethylamine and pyridine or in the presence of inorganic bases such as potassium carbonate and sodium hydrogen carbonate, in an inert solvent, in the presence of a transition metal catalyst (see Tetrahedron Letters 26, 1109(1985)). Examples of a transition metal catalyst include a zero-valent palladium reagent, which may be prepared in the reaction system, for example, by using a divalent palladium such as palladium (II) acetate, and a ligand such as triphenylphosphine or 2,2'-bis(diphenylphosohino)-1,1-binaphthyl (BINAP). It is also possible to directly use a zero-valent palladium reagent such as tetrakis(triphenylphosphine)palladium(0). Examples of the inert solvent include hydrocarbon type solvents such as benzene, toluene and hexane; ether type solvents such as tetrahydrofuran, diethyl ether and 1,2-dimethoxyethane; acetonitrile; N,N-dimethylformamide; or a mixture of these solvents. Step 2 may be carried out, for example, at room temperature. A preferred example of Step 2 is to synthesize compound (3) by reacting compound (2) with carbon monoxide and $R^2OH$ at room temperature, in N,N-dimethylformamide, in the presence of palladium(II) acetate, diisopropylethylamine and triphenylphosphine.

Step 3: Compound (4) may be prepared by oxidizing compound (3) into diol by means of a common diol-formation reaction with osmium tetraoxide, etc (see M. Hudlicky, "Oxidations in Organic Chemistry") or by means of a Sharpless asymmetric cishydroxylation reaction (Sharpless AD) with AD-mix as the reagent (see Tetrahedron Asymmetry 4, 133(1993), J. Org. Chem. 57, 2768(1992), J. Org. Chem. 61, 2582(1996)), in an inert solvent. Examples of the inert solvent include alcohol type solvents such as t-butylalcohol; hydrocarbon type solvents such as benzene, toluene and hexane; ether type solvents such as tetrahydrofuran, diethyl ether and 1,2-dimethoxyethane; acetonitrile; acetone; N,N-dimethylformamide; water; or a mixture of these solvents. Step 3 may be carried out, for example, at room temperature. A preferred example of Step 3 is to synthesize compound (4) by oxidizing compound (3) into diol with osmium tetraoxide at room temperature in a mixture of acetonitrile and water.

Step 4: Compound (5) may be prepared, for example, by reacting compound (4) with thionyl chloride in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile, or a mixture of these solvents, in the presence or absence of organic bases such as triethylamine, N-methylmorpholine, diisopropylethylamine and pyridine or of inorganic bases such as potassium carbonate and sodium hydrogen carbonate, followed by oxidation with a common oxidating agent such as hydrogen peroxide, OXONE® or ruthenium trichloride-sodium metaperiodate (see M. Hudlicky, "Oxidations in Organic Chemistry") in an inert solvent, examples of which include hydrocarbon type solvents such as benzene, toluene and hexane, halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents. A preferred example of Step 4 is to sythesize compound (5) by reacting compound (4) with thionyl chloride for 0.5 to 2 hours at 0 to 20° C., in a solvent of dichloromethane, in the presence of triethylamine, followed by oxidation with ruthenium trichloride-sodium metaperiodate as the oxidizing agent, for 0.5 to 2 hours at 0° C. to room temperature, in a mixture of carbon tetrachloride, acetonitrile and water.

Step 5: Compound (6) may be prepared, for example, by reacting compound (5) with sodium azide in an inert solvent, examples of which include ether type solvents such as tetrahydrofuran; ketones such as acetone; N,N-dimethylformamide; water; or a mixture of these solvents, followed by hydrolysis (see J. Am. Chem. Soc. 110, 7538(1988)). A preferred example of Step 5 is to yield intermediate compound (6) by reacting compound (5) with sodium azide for 1 to 20 hours at room temperature to 50° C., in a mixture of N,N-dimethylformamide and water, followed by hydrolysis with 20% sulfuric acid for 1 to 2 days, in a mixture of ether and water.

Compound (9) may be prepared from the obtained synthetic intermediate (6) by inverting the hydroxyl group of compound (7), which has a relative stereo structure represented by formula [II] wherein $R^1$ and $R^2$ represents something other than a hydrogen atom, according to Steps 6 and 7 below. Therefore, it is possible to prepare a compound which has the desired relative stereo structure even in the case where the subtituent at the 3 position is introduced by means of a stereo inversion on the 3 position carbon atom.

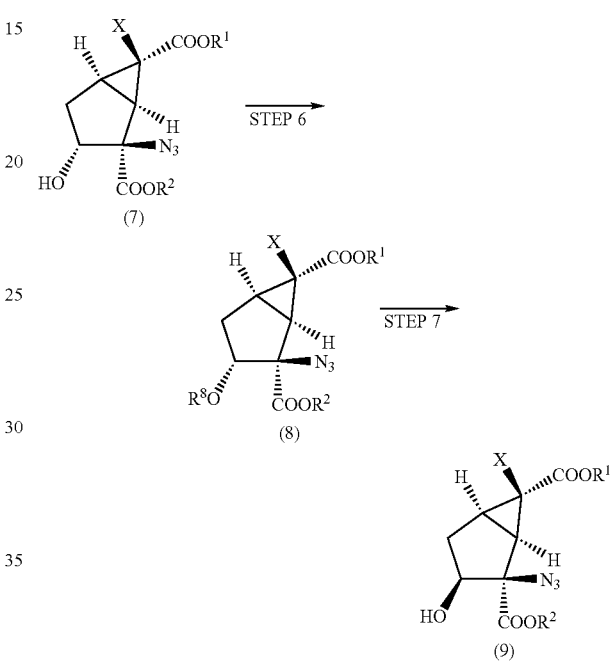

Step 6: Compound (8) may be prepared from compound (7) wherein $R^1$ and $R^2$ represent something other than a hydrogen atom, for example, by reacting the hydroxyl group of compound (7) with a trifluoromethanesulfonylating agent such as trifluoromethane sulfonic acid anhydride or N-phenyl-bis(trifluoromethanesulfonimide), or with a alkyl- or aryl sulfonylating agent such as methane sulfonyl chloride, benzene sulfonyl chloride or toluene sulfonyl chloride, in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence of inorganic bases such as sodium hydride, potassium hydride, sodium carbonate, potassium carbonate, sodium hydroxide and potassium hydroxide; metal amides such as lithium bis(trimethylsilyl)amide, lithium diisopropylamide and sodium amide; organic bases such as triethylamine, pyridine, diisopropylethylamine, 4-(N,N-dimethylamino)pyridine and 2,6-di-t-butylpyridine; bases such as potassium t-butoxide. A preferred example of Step 6 is to sythesize compound (8) by reacting compound (7) with trifluoromethane sulfonic acid anhydride for 0.5 to 3 hours at −78° C. to ice-cooled temperature, in a solvent of dichloromethane, in the presence of pyridine.

Step 7: Compound (9) may be prepared, for example, by reacting compound (8) with an alkali hydroxide such as potassium hydroxide or sodium hydroxide; a nitrite salt such as potassium nitrite (see Tetrahedron Lett., 3183 (1975)); or potassium superoxide (see Tetrahedron Lett. 34, 8029 (1993)), in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide, N-methyl-2-pyrrolidinone; alcohol type solvents such as dimethylsulfoxide, methanol and ethanol; water; or a mixture of these solvents, in the presence or absence of crown ether.

Moreover, it is also possible to prepare compound (9) directly from compound (7) by means of a Mitsunobu reaction with a benzoic acid derivative, in the presence of a dehydrocondensing agent such as diethylaxodicarboxylic acid or triphenylphosphine (see D. L. Hughes, OR, 42, 335 (1992)).

A preferred example of Step 7 is to sythesize compound (9) by reacting compound (8) with potassium nitrite for 2 to 6 days at room temperature to 45° C., in N,N-dimethylformamide, in the presence of 18-crown 6-ether.

Compounds (15) and (16), which are the compounds of the present invention, may be prepared according to Steps 8, 9, 10, 11, 12 and 13 below from synthetic intermediates (6) represented by formula [I] wherein X represents a hydrogen atom or a fluorine atom and Y represents —$SR^3$, —$S(O)_nR$, —$SCHR^3R^4$ or —$S(O)_nCHR^3R^4$.

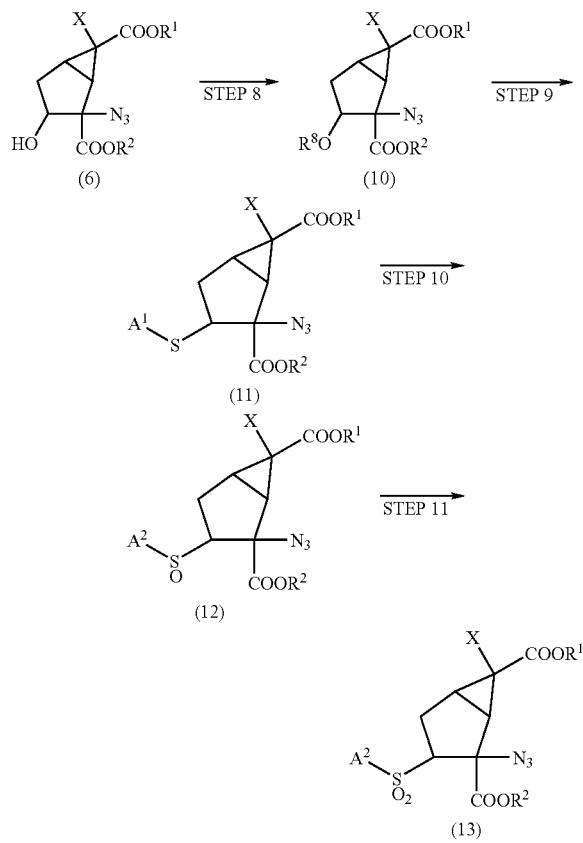

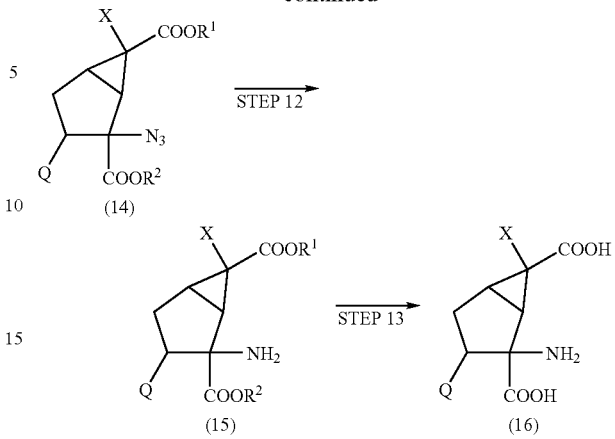

Step 8: Compound (10) may be prepared by means of the same method as the Step 6 by converting the hydroxyl group of compound (6) wherein $R^1$ and $R^2$ represent something other than a hydrogen atom. A preferred example of Step 8 is to prepare compound (10) by reacting the hydroxyl group of compound (6) with trifluoromethane sulfonic acid anhydride for 30 minutes to 3 hours at −78° C. to ice-cooled temperature, in dichloromethane, in the presence of pyridine.

Step 9: Compound (11) may be prepared, for example, by reacting compound (10) with a compound represented by -$A^1$SNa, -$A^1$SK, etc, which is prepared from metal alcoholates such as sodium ethoxide and potassium t-butoxide; sodium; potassium; sodium hydride; potassium hydride; and mercaptans or thiophenols represented by -$A^1$SH, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; dimethylsulfoxide; N,N-dimethylformamide; or a mixture of these solvents. A preferred example of Step 9 is to prepare compound (11) by reacting compound (10) with a compound represented by -$A^1$SNa, which is prepared from sodium and a compound represented by -$A^1$SH, for 10 minutes to 1 hour at room temperature, in dimethylsulfoxide.

Step 10: Compound (12) may be prepared from compound (11) wherein $A^1$ represents something other than a hydrogen atom, for example, by means of a common oxidation reaction in which a sulfide is converted into a sulfoxide with sodium periodic acid, peracetic acid, etc (see M. Hudlicky, "Oxidations in Organic Chemistry"), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; dimethylsulfoxide; N,N-dimethylformamide; methanol; ethanol; acetic acid; water; or a mixture of these solvents.

Step 11: Compound (13) may be prepared from compound (12) or from compound (11) wherein $A^1$ represents something other than a hydrogen atom, for example, by means of a common oxidation reaction in which a sufide or a sulfoxide is converted into a sulfine with 3-chloroperbenzoic acid, hydrogen peroxide, etc (see M. Hudlicky, "Oxidations in Organic Chemistry"), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; dimethylsulfoxide; N,N-dimethylformamide; water; or a mixture of these solvents. It is also possible to yield a mixture of compound (12) and compound (13) from compound (11) wherein $A^1$ represents something other than a hydrogen atom, by using a common oxidizing agent such as 3-chloroperbenzoic acid or hydrogen peroxide (see M. Hudlicky, "Oxidations in Organic Chemistry"), and by controlling the reaction conditions such as the amount, reaction time, reaction temperature and solvent of the oxidizing agent, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; dimethylsulfoxide; N,N-dimethylformamide; water; or a mixture of these solvents. A preferred example of Step 11 is to prepare compound (12) and compound (13) by reacting compound (11) with 3-chloroperbenzoic acid for 1 to 24 hours at −78° C. to room temperature, in dichloromethane.

Step 12: Compound (15) a compound of the present invention, may be prepared from compound (14), for example, by means of a common reduction reaction of an azide group, typical examples of which include: (a) Staudinger reaction with triethyl phosphite, trimethylphosphine, tributyl phosphine, triphenylphosphine, etc (see Bull. Chem. Soc. Fr., 815(1985)), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents; (b) hydrogenation in an inert solvent, examples of which include alcohols such as ethanol and methanal; esters such as ethyl acetate; N,N-dimethylformamide; water; or a mixture of these solvents, in the presence of a metal catalyst such as palladium/carbon or palladium black; and (c) hydride reduction with lithium aminoborohydride, etc (see A. F. Abdel-Magid, "Reductions in Organic Synthesis"). A preferred example of Step 12 is to prepare compound (15) by reacting compound (14) by means of a Staudinger reaction with trimethylphosphine for 1 to 2 hours at room temperature, in a mixture of tetrahydrofuran and water.

Step 13: Compound (16), which is a compound of the present invention, may be prepared from compound (15) wherein at least one of $R^1$ and $R^2$ represents something other than a hydrogen atom, for example, by converting the moieties represented by —COOR$^1$ and —COOR$^2$ of compound (15) into carboxylic acid by means of a common hydrolysis reaction (see T. W. Greene, P. G. M. Wuts, "Protective Groups in Organic Synthesis"). A preferred example of Step 13 is to prepare compound (16), which is a synthetic intermediate of the compounds of the present invention, by hydrolyzing compound (15) with lithium hydroxide for 5 to 7 days at room temperature to 40° C., in a mixture of tetrahydrofuran and water. Another preferred example of Step 13 is to prepare compound (16) of the present invention by hydrolyzing compound (15) with 60% sulfuric acid for 1 to 5 days at 100° C. to 150° C.

Also, compounds (18) and (19), which are compounds of the present invention, may be prepared according to Steps 14, 15 and 16 below from intermediates (10) yielded in Step 8 which are represented by formula [I] wherein X represents a hydrogen atom or a fluorine atom and Y represents —NH$_2$.

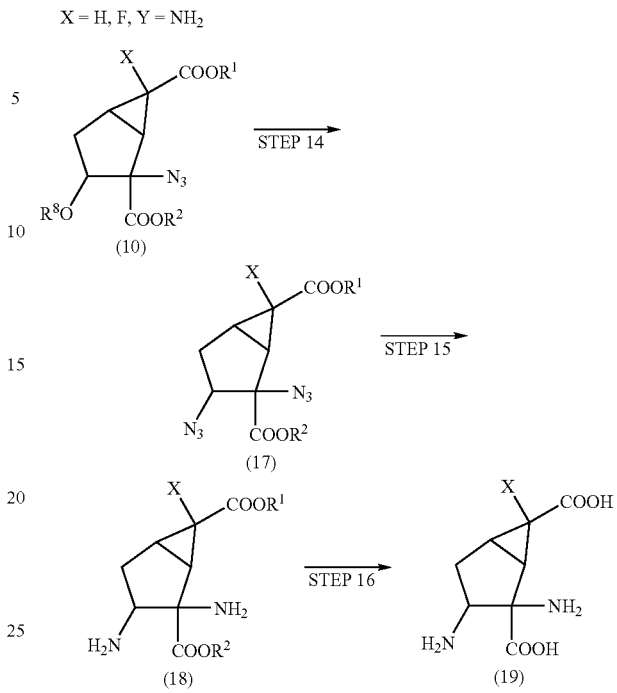

Step 14: Compound (17) may be prepared by reacting compound (10) with sodium azide in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether, 1,2-dimethoxyethane; ethyl acetate; acetonitrile; acetone; dimethylsulfoxide; N,N-dimethylformamide; water; or a mixture of these solvents. A preferred example of Step 14 is to prepare compound (17) by reacting compound (10) with sodium azide for 0.5 to 2 hours at room temperature, in N,N-dimethylformamide.

Step 15: Compound (18), which is a compound of the present invention, may be prepared by hydrolyzing the two azide groups of compound (17) by means of the same method as Step 12. A preferred example of Step 15 is to prepare compound (18) by reacting compound (17) for 1 to 2 days at room temperature, under hydrogen atmosphere, in a mixture of acetic acid and water, in the presence of 10% palladium carbon.

Step 16: Compound (19), which is a compound of the present invention, may be prepared from compound (18) wherein at least one of $R^1$ and $R^2$ represents something other than a hydrogen atom by hydrolyzing the moieties represented by —COOR$^1$ and —COOR$^2$ of compound (18) by means of the same method as Step 13. A preferred example of Step 16 is to prepare compound (19) of the present invention by hydrolyzing compound (18) with lithium hydroxide for 1 to 7 days at room temperature, in a mixture of tetrahydrofuran and water.

Compounds (26), (27), (29) and (30), which are the compounds of the present invention, may be prepared from synthetic intermediate (6) represented by formula [I] wherein X represents a hydrogen atom or a fluorine atom and Y represents —NHCHR$^3$R$^4$ or —N(CHR$^3$R$^4$)(CHR$^5$R$^6$), according to Steps 17, 18, 19, 20, 21, 22 and 23 below.

X = H, F, Y = N(CHR³R⁴)(CHR⁵R⁶)

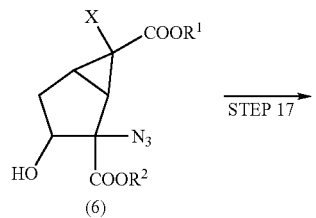
(6)

STEP 17 →

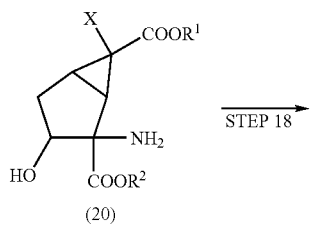
(20)

STEP 18 →

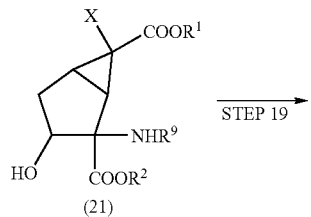
(21)

STEP 19 →

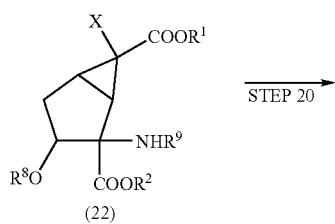
(22)

STEP 20 →

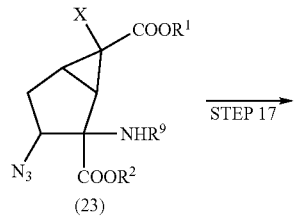
(23)

STEP 17 →

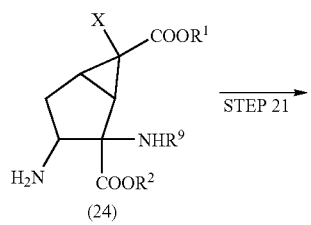
(24)

STEP 21 →

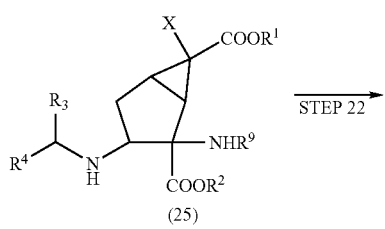
(25)

STEP 22 →

-continued

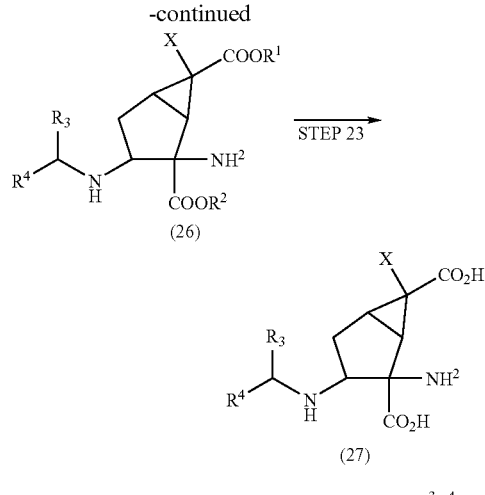
(26)

STEP 23 →

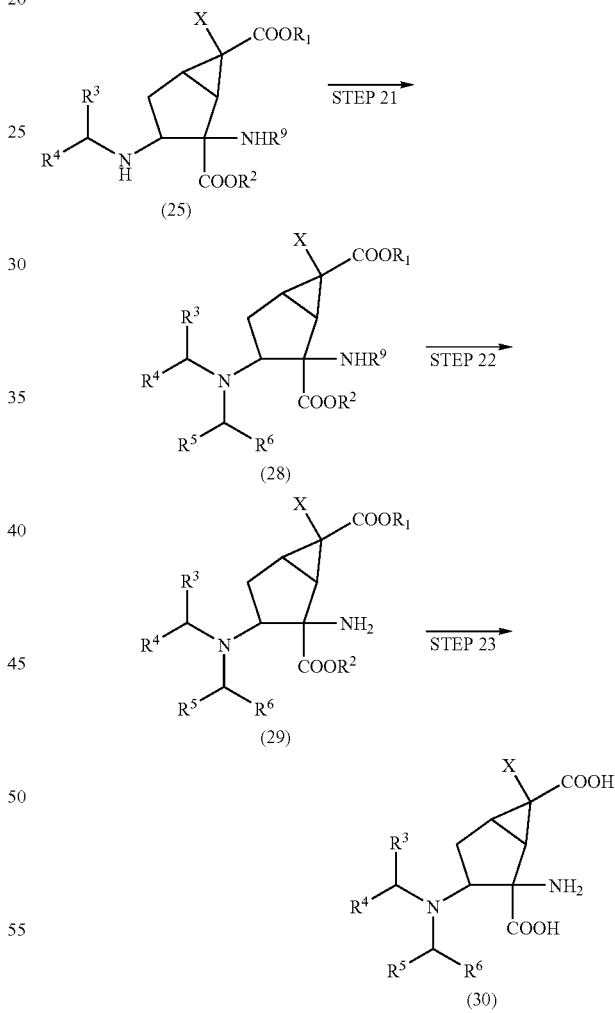

Step 17: Compounds (20) and (24) may be prepared by reducing the azide groups of compounds (6) and (23), respectively, by means of the same method as Step 12. A preferred example of Step 17 is to prepare compound (20) and compound (24) by reacting compound (6) and compound (23) by means of a Staudinger reaction with trimethylphosphine for 1 to 12 hours at room temperature, in a mixture of tetrahydrofuran and water.

Step 18: Compound (21) may be prepared by converting the amino group of compound (20) by means of a common protection reaction of an amino group (see T. W. Greene, P. G M. Wuts, "Protective Groups in Organic Synthesis"). A preferred example of the protection reaction of an amino group in Step 18 is to prepare compound (21) by reacting compound (20) with di-t-butyldicarbonate for 2 to 6 hours at room temperature, in tetrahydrofuran, in the presence of a saturated aqueous solution of sodium hydrogen carbonate.

Step 19: Compound (22) may be prepared by alkyl- and aryl-sulfonylating the hydroxyl group of compound (21) wherein $R^1$ and $R^2$ represents something other than a hydrogen atom by means of the same method as Step 6. A preferred example of Step 19 is to prepare compound (22) by reacting the hydroxyl group of compound (21) with trifluoromethane sulfonic acid anhydride for 30 minutes to 2 hours at −78° C. to ice-cooled temprature, in dichloromethane, in the presence of pyridine.

Step 20: Compound (23) may be prepared, for example, by reacting compound (22) with sodium azide in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; ethyl acetate; acetonitrile; acetone; dimethylsulfoxide; N,N-dimethylformamide; water; or a mixture of these solvents. A preferred example of Step 20 is to prepare compound (23) by reacting compound (22) with sodium azide for 1 to 2 days at room temperature to 35° C., in N,N-dimethylformamide.

Step 21: Compounds (25) and (28) may be prepared, for example, by reacting the amino groups represented by —NH$_2$ and —R$^3$R$^4$CHNH of compounds (24) and (25), respictively, with a compound represented by R$^3$R$^4$CHZ or R$^5$R$^6$CHZ, in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence or absence of inorganic bases such as sodium hydride, potassium hydride, potassium carbonate, sodium carbonate, sodium hydrogen carbonate, sodium hydroxide and potassium hydroxide; metal amides such as lithium bis(trimethylsilyl)amide, lithium diisopropylamide amd sodium amide; organic bases such as triethylamine, pyridine, diisopropylethylamine, 4-(N,N-dimethylamino)pyridine and 2,6-di-t-butylpyridine; and bases such as poatassium t-butoxide. In this case, Z represents a leaving group, for example, a halogen atom, tosylsulfonate, trifluoromethansulfonate or tolylsulfonate. Moreover, it is also possible to prepare compounds (25) and (28), for example, by means of a reductively aminating compounds (24) and (25), respectively, by means of a Borch reaction in which compounds (24) and (25) are reacted with a compound represented by R$^3$COR$^4$ or by R$^5$COR$^6$ (see A. F. Abdel-Magid et al., Tetrahedron Lett., 31, 5595 (1990)), in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; ethanol; methanol; water; or a mixture of these solvents, in the presence of a reducing agent such as sodium triacetoxy borohydride or sodium cyanotrihydroborate. A preferred example of Step 21 is to prepare compound (25) by reacting compound (24) with a compound represented by R$^3$R$^4$CHBr for 1 to 4 days at room temperature, in chloroform, in the presence of pyridine. Another preferred example of Step 21 is to prepare compound (28) by reacting compound (25) with a compound represented by R$^5$R$^6$CHI for 1 to 4 days at room temperature, in N,N-dimethylformamide, in the presence of potassium carbonate.

Step 22: Compounds (26) and (29) may be prepared by deprotecting R$^9$, which is the protecting group for the amino group of compound (25) and compound (28), by means of a common deprotection reaction (see T. W. Greene, P. G. M. Wuts, "Protective Groups in Organic Synthesis"), and converting R$^9$ into an amino group. A preferred example of Step 22 is to prepare compound (26) and compound (29) by deprotecting compound (25) and compound (28) with 4N hydrogen chloride/ethyl acetate for 12 to 36 hours at ice-cooling to room temperature.

Step 23: Compounds (27) and (30), which are compounds of the present invention, may be prepared from compounds (26) and (29) wherein at least one of $R^1$ and $R^2$ represents something other than a hydrogen atom, by hydrolyzing the moieties represented by —COOR$^1$ and —COOR$^2$ of compounds (26) and (29) by means of the same method as Step 13. A preferred example of Step 23 is to prepare compound (27) and compound (30) of the present invention by hydrolyzing compound (26) and compound (29) with lithium hydroxide for 1 to 7 days at room temperature, in a mixture of tetrahydrofuran and water. Compounds (32) and (33), which are compounds of the present invention, may be prepared from compound (24) represented by formula [I] wherein, X represents a hydrogen atom or a fluorine atom, and Y represents —NHCOR$^3$, according to Steps 24, 25 and 26 below.

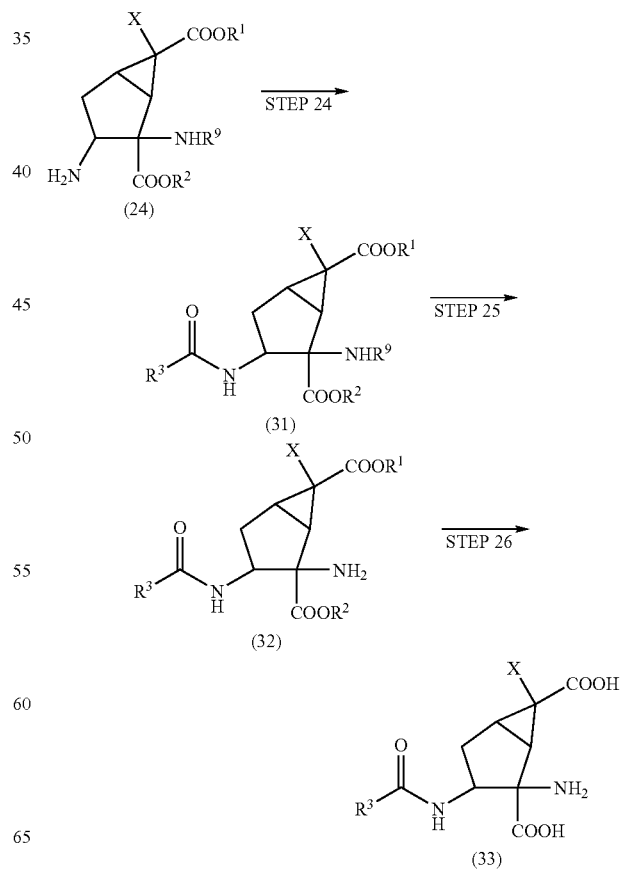

Step 24: Compound (31) may be prepared, for example, by reacting the 3-position amino group of compound (24) with a compound represented by ZCOR⁷ or R⁷COOCOR⁷, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence or absence of organic bases such as triethylamine, pyridine, morpholine, diisopropylethylamine, 4-(N,N-dimethylamino)pyridine and 2,6-di-t-butylpyridine. In this case, Z represents a leaving group, for example, a halogen atom, an ethoxycarbonyloxy group or a phenoxycarbonyloxy group. Or, in the case where $R^3$ represents a hydrogen atom, compound (31) may be prepared by means of a common formylation reaction (see T. W. Greene, P. G. M. Wuts, "Protective Groups in Organic Synthesis"). A preferred example of Step 25 is to prepare compound (31) by reacting compound (24) with a compound represented by $R^3COCl$ for 1 to 4 hours at room temperature, in chloroform, in the presence of pyridine.

Step 25: Compound (32), which is a compound of the present invention, may be prepared from compound (31) by means of the same deprotection reaction of —NHR⁹ as Step 22. A preferred example of Step 25 is to prepare compound (32) by deprotecting compound (31) with 4N hydrogen chloride/ethyl acetate for 30 minutes to 2 hours at ice-cooled temperature.

Step 26: Compound (33), which is a compound of the present invention, may be prepared from compound (32) wherein at least one of $R^1$ and $R^2$ represents something other than a hydrogen atom, by means of the same hydrolysis reaction of —COOR¹ and —COOR² as Step 13. A preferred example of Step 26 is to prepare compound (33) of the present invention by hydrolyzing compound (32) with lithium hydroxide for 1 to 7 hours at room temperature, in a mixture of tetrahydrofuran and water.

Compounds (35) and (36) of the present invention may be prepared from synthetic intermediate (6) wherein $R^2$ represents a benzyl group represented by formula [I] wherein, X represents a hydrogen atom or a fluorine atom and Y represents —OCOR⁷, according to Steps 27, 28 and 29 below.

X = H, F, Y = OCOR⁷, R² = Bn

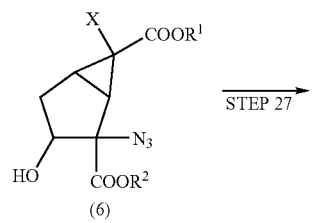
(6)

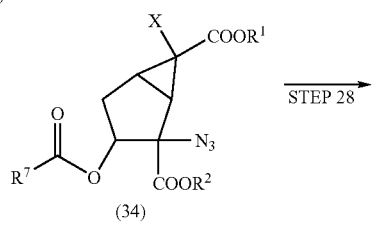
(34)

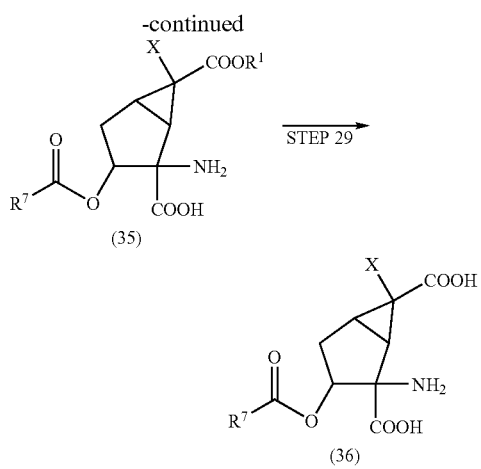

Step 27: compound (34) may be prepared from compound (6) wherein $R^1$ represents something other than a hydrogen atom and $R^2$ represents a benzyl group, for example, by reacting the hydroxyl group of compound (6) with a compound represented by ZCOR⁷ or by R⁷COOCOR⁷, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence or absence of organic bases such as triethylamine, pyridine, morpholine, diisopropylethylamine, 4-(N,N-dimethylamino)pyridine and 2,6-di-t-butylpyridine. In this case, Z represents a leaving group, for example, a halogen atom, an ethoxycarbonyloxy group or a phenoxycarbonyloxy group. A preferred example of Step 27 is to prepare compound (34) by reacting compound (6) with a compound represented by R⁷COCl for 12 to 36 hours at room temperature, in pyridine.

Step 28: Compound (35), which is a compound of the present invention, may be prepared from compound (34), for example, by yielding an amino body by means of a Staudinger reaction with triethyl phosphite, trimethylphosphine, tributyl phosphine, triphenylphosphine, etc (see Bull. Chem. Soc. Fr., 815(1985)), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents, and then, for example, by further reductively deprotecting the benzyl group of the obtained amino body by means of a hydrogenation reaction in the presence of a metal catalyst such as palladium/carbon or palladium black, in an inert solvent, examples of which include alcohols such as ethanol and methanol; esters such as ethyl acetate; N,N-dimethylformamide; water; or a mixture of these solvents. It is also possible to prepare compound (35) directly from compound (34), for example, by means of a hydrogenation reaction in the presence of a metal catalyst such as palladium/carbon or palladium black, in an inert solvent, examples of which include alcohols such as ethanol and methanol; esters such as ethyl acetate; N,N-dimethylformamide; water; or a mixture of these solvents. A preferred example of Step 28 is to prepare compound (35) as follows: An amine body is prepared by reacting compound (34) by means of a Staudinger reaction with trimethylphosphine for 30 minutes to 2 hours at room temperature, in a mixture of tetrahydrofuran and water. And then compound (35) is prepared by reacting this amine body for 30 minutes to 2 hours at room temperature, in ethanol, in the presence of 5% palladium carbon under hydrogen atmosphere.

Step 29: Compound (36) of the present invention may be prepared from compound (35) by means of the same method as Step 13. A preferred example of Step 29 is to prepare compound (36) by hydrolyzing compound (35) with lithium hydroxide for 30 minutes to 2 hours at room temperature, in a mixture of tetrahydrofuran and water.

Also, monoester derivative (38), which is a compound of the present invention, may be prepared from compound (37) of the present invention wherein $R^1$ and $R^2$ each represent a hydrogen atom, according to Step 30 below. Moreover, compound (40) of the present invention, which is a monoester derivative, may be prepared from compound (39) wherein $R^1$ and $R^2$ each represent something other than a hydrogen atom, according to Step 31 below.

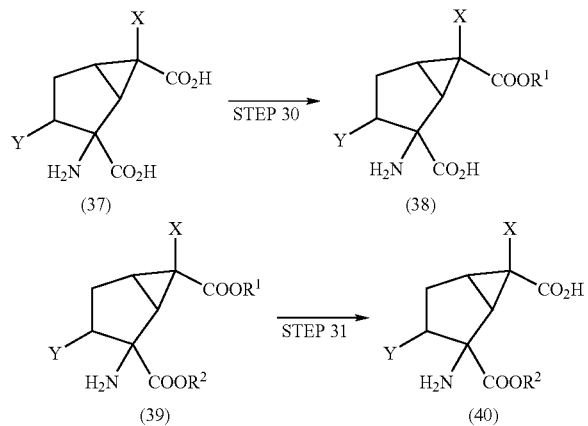

Step 30: Compound (38), which is a compound of the present invention, may be prepared by esterifying the carboxylic moiety on the 6-position carbon of compound (37) by means of a common esterification reaction (see T. W. Greene, P. G. M. Wuts, "Protective Groups in Organic Synthesis") A preferred example of Step 30 is to prepare compound (38) of the present invention by reacting compound (37) for 1 to 5 hours at ice-cooling to 50° C., in the presence of $R^1OH$ and thionyl chloride.

Step 31: Compound (40) of the present invention may be prepared from compound (39) wherein $R^1$ and $R^2$ each represents something other than a hydrogen atom, by converting the moiety represented by —$COOR^1$ of compound (39) into carboxylic acid by means of a common hydrolysis reaction (see T. W. Greene, P. G. M. Wuts, "Protective Groups in Organic Synthesis"), for a short period of time or at a low temperature. A preferred example of Step 31 is to prepare compound (40) of the present invention by hydrolyzing the moiety represented by —$COOR^1$ of compound (39) with lithium hydroxide for 30 minutes to 3 hours at 0° C. to room temperature, in a mixture of tetrahydrofuran and water.

In the present invention, the compound that antagonizes Group II metabotropic glutamate receptors means a compound which shows a concentration-dependant antagonistic effect in a receptor binding test with cells expressing mGluR2 and mGluR3, respectively, by means of the method described in "Mol Pharmacol, 53, 228-233, 1998"; shows the affinity to mGluR2/R3 the same as or higher than that of glutamic acid; and forever shows an antagonistic effect on gultamic acid-induced GTPγS binding, in the GTPγS binding assay. Or, it means a compound which shows an antagonistic effect to the inhibitory action of glutamatic acid on the forskolin-stimulated cAMP accumulation.

The compounds of the present invention may be incorporated into pharmaceutical formulations or pharmaceutical compositions by being combined with one or more pharmaceutically acceptable carriers, excipients or diluents. Examples of the carriers, excipients and diluents include water, lactose, dextrose, fructose, sucrose, sorbitol, mannitol, polyethylene glycol, propylene glycol, starch, gum, gelatin, arginate, calcium silicate, calcuim phosphate, cellulose, water syrup, methylcellulose, polyvinyl pyrrolidone, alkyl parahydroxybenzoate, talc, magnesuim stearate, stearic acid, glycerol and oils such as sesame oil, olive oil and soybean oil.

By means of common formulation procedures the compounds of the present invention may be formulated into drugs for oral or parenteral administrations, in particular, as Group II metabotropic glutamate receptor antagonists, in the form of tablets, pills, capsules, granules, powders, liquids, emulsions, suspensions, ointments, injections and skin plasters by mixing with the above mentioned carriers, excipients or diluents, and, if necessary, further mixing with additives such as commonly used fillers, binders, disintegrants, pH regulators and solubilizers.

The compounds of the present invention can be administered orally or parenterally to an adult patient in a quantity of 0.01 to 500 mg per day in a single dose or in several doses. Oral adimistration is preferred from the point of usability and medicinal benefits. The dosage can be increased or decreased as appropriate according to the type of the disease targeted for treatment, and the age, weight and symptoms of the patient.

In the following are shown examples of the synthesis and the pharmacological tests of the compounds of the present invention in detail. It should be understood that the availability of the compounds of the present invention is not limited to these examples.

REFERENCE EXAMPLE 1

Synthesis of (1R,2R,3R,5R,6R)-2-azido-6-fluoro-3-hydroxy-bicyclo[3.1.0]hexane-2,6-dicarboxylic acid diethyl ester (1) 245 mL of a solution of 2.66 M n-butyllithiumhexane was added dropwise to 700 mL of a solution of tetrahydrofuran containing 137 mL of hexamethyldisilazane and stirred for 1 hour at a temperature maintained at −63° C. to −54° C. 340 mL of a solution of tetrahydrofuran containing 101 g of (1R,5R,6R)-6-fluoro-2-oxobicyclo[3.1.0]hexane-6-carboxylic acid ethyl ester was added dropwise thereto at a temperature maintained at −63° C. to −52° C. 700 mL of a solution of tetrahydrofuran containing 213 g of N-phenyl-bis(trifluoromethanesulfonimide) was added thereto 1 hour later at 63° C. to −45° C. The reaction solution was warmed naturally to room temperature and further stirred for 2.5 hours. The reaction solution was diluted with diethyl ether, washed three times with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200 (made by Wako Pure Chemical Industries Ltd.), eluent: hexane-ethyl acetate=30:1 to 20:1 to 5:1). The obtained 175 g of (1R,5R,6R)-6-fluoro-2-trifluoromethane-sulfonyloxybicyclo[3.1.0]hex-2-ene-6-carboxylic acid ethyl ester was dissolved in 875 mL of N,N-dimethylformamide and 875 mL of ethanol, and after 95.1 mL of diisopropyl-ethylamine, 8.65 g of triphenylphosphine and 3.70 g of palladium acetate were added thereto, the mixture was stirred for 5.5 hours at room temperature, under a carbon monoxide atmosphere. 1N hydrochloric acid was added thereto, and the reaction solution was extracted six times with diethyl ether. The organic layers were combined, washed four times with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200 (made by Wako Pure Chemical Industries Ltd.), eluent: hexane-ethyl acetate=30:1 to 20:1 to 10:1), thereby yielding 92.6 g of (1R,5R,6R)-6-fluoro-bicyclo [3.1.0]hex-2-ene-2,6-dicarboxylic acid diethyl ester.

$^1$H-NMR(200 MHz, CDCl$_3$)δ(ppm); 1.31 (t, J=7.0 Hz, 3H), 1.33 (t, J=7.0 Hz, 3H), 2.37-2.51 (m, 1H), 2.65-2.81 (m, 1H), 2.88-3.04 (m, 1H), 3.10 (dd, J=7.5, 2.6 Hz, 1H), 4.12-4.40 (m, 4H), 6.77-6.79 (m, 1H).

MS(ESI)(Pos)m/z; 265 (M+Na)$^+$ $[α]_D^{21}$=+158.0° (CHCl$_3$, c=1.5)

(2) 160 mL of an aqueous solution of 50% N-methylmorpholine N-oxide and 121 mL of an aqueous solution of 4% osmium oxide (VIII) were added to 92.4 g of (1R,5R,6R)-6-fluoro-bicyclo[3.1.0]hex-2-ene-2,6-dicarboxylic acid diethyl ester dissolved in 1.76 L of acetonitrile and 680 mL of water, and the mixture was stirred for 1 hour at room temperature. After sodium sulfite was added thereto at ice-cooled temperature, the reaction solution was stirred for 30 minutes at room temperature and then filtered through celite. A saturated aqueous solution of sodium chloride was added thereto, and the filtrate was extracted twice with ethyl acetate. The organic layers were combined, washed with a saturated aqueous solution of sodium chloride and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=4:1 to 1:1), thereby yielding 95.6 g of (1R,2S,3R,5R,6R)-6-fluoro-2,3-dihydroxybicyclo[3.1.0]hexane-2,6-dicarboxylic acid diethyl ester.

$^1$H-NMR(200 MHz, CDCl$_3$)δ(ppm); 1.31 (t, J=7.3 Hz, 6H), 2.03-2.34 (m, 3H), 2.40-2.55 (m, 1H), 2.70 (d, J=9.2 Hz, 1H), 4.09 (s, 1H), 4.18-4.47 (m, 5H).

MS(ESI)(Nega)m/z; 275 (M−H)$^-$ $[α]_D^{27}$=−69.1° (CHCl$_3$, c=1.4)

(3) 106 mL of triethylamine was added to 1.24 L of a solution of dichloromethane containing 95.4 g of (1R,2S,3R,5R,6R)-6-fluoro-2,3-dihydroxybicyclo[3.1.0]hexane-2,6-dicarboxylic acid diethyl ester, And after 37.6 mL of thionyl chloride was added dropwise thereto, the mixture was stirred for 30 minutes at ice-cooling. The reaction solution was washed twice with water and with a saturated aqueous solution of sodium chloride, and then dried over anhydrous magnesium sulfate. The desiccant was filtered off, and the filtrate was concentrated under reduced pressure. The residue was dissolved in 640 mL of carbon tetrachloride, 640 mL of acetonitrile and 760 mL of water. 96.0 g of sodium metaperiodate and 655 mg of ruthenium trichloride hydrate were added thereto, and the solution was stirred for 1 hour at room temperature. After the mixture was filtered through celite, the filtrate was separated, and the aqueous layer was extracted with diethyl ether. The organic layers were combined, washed with a saturated aqueous solution of sodium chloride, and then dried over anhydrous magnesium sulfate. After the desiccant was filtered off, the filtrate was concentrated under reduced pressure, and the residue was purified by column chromatography (silica gel: Wako gel C200, eluent: hexane-ethyl acetate=4:1), thereby yielding 109 g of (1R,1aR,1bS,4aR,5aR)-1-fluoro-3,3-dioxotetrahydro-2,4-dioxa-3

λ$^6$-thiacyclopropa[a]pentalene-1,1b-dicarboxylic acid diethyl ester.

$^1$H-NMR(200 MHz, CDCl$_3$)δ(ppm); 1.33 (t, J=7.0 Hz, 3H) 1.34 (t, J=7.0 Hz, 3H), 2.52-2.94 (m, 4H), 4.23-4.47 (m, 4H), 5.40-5.53 (m, 1H).

MS(ESI)(Pos)m/z; 361 (M+Na)$^+$ $[α]_D^{28}$=+18.3° (CHCl$_3$, c=1.0)

(4) 37.7 g of sodium azide was added to 109 g of (1R,1aR,1bS,4aR,5aR)-1-fluoro-3,3-dioxotetrahydro-2,4-dioxa-3λ$_6$-thiacyclopropa[a]pentalene-1,1b-dicarboxylic acid diethyl ester dissolved in 1.10 L of N,N-dimethylformamide and 110 mL of water, and the mixture was stirred for 14 hours at 50° C. The solvent was distilled off under reduced pressure, and after the residue was dissolved in 6.48 L of diethyl ether and 177 mL of water, 516 mL of 20% (V/V) sulfuric acid was added thereto, and the mixture was stirred for 34 hours at room temperature. After the reaction solution was separated, the organic layers were twice washed with a saturated aqueous solution of sodium chloride and then dried over anhydrous magnesium sulfate. After the desiccant was filtered off, the filtrate was concentrated under reduced pressure, and the residue was purified by column chromatography (silica gel: Wako gel C200, eluent: hexane-ethyl acetate=4:1), thereby yielding 88.5 g of (1R,2R,3R,5R,6R)-2-azido-6-fluoro-3-hydroxy-bicyclo[3.1.0]hexane-2,6-dicarboxylic acid diethyl ester.

$^1$H-NMR (200 MHz, CDCl$_3$)δ(ppm); 1.33 (t, J=7.0 Hz, 3H), 1.38 (t, J=7.0 Hz, 3H), 2.18-2.61 (m, 5H), 4.21-4.48 (m, 5H).

MS(ESI)(Pos)m/z; 324 (M+Na)$^+$ $[α]_D^{22}$=−48.7° (CHCl$_3$, c=1.0)

EXAMPLE 1

Synthesis of (1R,2R,3S,5R,6R)-2-azido-6-fluoro-3-hydroxy-bicyclo[3.1.0]hexane-2,6-dicarboxylic acid diethyl ester (1) 48 μL of pyridine and 78 μL of trifluoromethane sulfonic acid anhydride dissolved in 0.4 mL of dichloromethane were added dropwise to 120 mg of (1R,2R,3R,5R,6R)-2-azido-6-fluoro-3-hydroxy-bicyclo[3.1.0]hexane-2,6-dicarboxylic acid diethyl ester dissolved in 20 mL of dichloromethane at −75° C., and the mixture was stirred for 1.5 hours at ice-cooling under a nitrogen atmosphere. 24 μL of pyridine and 39 μL of trifluoromethane sulfonic acid anhydride dissolved in 0.2 mL of dichloromethane were added dropwise thereto at −75° C., and the mixture was stirred for 25 minutes at ice-cooling. 10 mL of ether was added thereto, and after the solids were filtered off, the filtrate was concentrated under reduced pressure, and the residue was purified by column chromatography (silica gel: Wako gel C200, eluent: hexane-ethyl acetate=5:1), thereby yielding 166 mg of (1R,2R,3R,5R,6R)-2-azido-6-fluoro-3-trifluoromethanesulfonyloxy-bicyclo[3.1.0]hexane-2,6-dicarboxylic acid diethyl ester.

$^1$H-NMR(200 MHz, CDCl$_3$)δ(ppm); 1.35 (t, J=7.0 Hz, 3H), 1.38 (t, J=7.0 Hz, 3H), 2.35-2.50 (m, 2H), 2.62-2.86 (m, 2H), 4.31 (q, J=7.0 Hz, 2H), 4.27-4.55 (m, 2H), 4.94-5.10 (m, 1H).

MS(FAB)(Pos)m/z; 434 (M+H)$^+$ $[α]_D^{26}$=−31.2° (CHCl$_3$, c=0.4)

(2) 688 mg of potassium nitrite and 428 mg of 18-crown 6-ether was added to 701 mg of (1R,2R,3R,5R,6R)-2-azido-6-fluoro-3-trifluoromethanesulfonyloxy-bicyclo[3.1.0]hexane-2,6-dicarboxylic acid diethyl ester dissolved in 6.9 mL of N,N-dimethylformamide, and the mixture was stirred for 1.5 days at room temperature and further stirred for 3.5 days at 45° C., under a nitrogen atmosphere. Water was added thereto, and the mixture was extracted twice with ethyl acetate. The organic layers were combined, washed with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=5:1), thereby yielding 388 mg of (1R,2R,3S,5R,6R)-2-azido-6-fluoro-3-hydroxy-bicyclo[3.1.0]hexane-2,6-dicarboxylic acid 2,6-diethyl ester.

$^1$H-NMR(200 MHz, CDCl$_3$)δ(ppm); 1.34 (t, J=7.0 Hz, 3H), 1.36 (t, J=7.0 Hz, 3H), 2.16 (dd, J=2.9 Hz, 14.9 Hz, 1H), 2.17-2.30 (m, 1H), 2.44 (dd, J=3.1, 8.1 Hz, 1H), 2.61 (dd, J=12.3, 16.0 Hz, 1H), 2.80-2.99 (m, 1H), 4.29 (q, J=7.0 Hz, 2H), 4.34 (q, J=7.0 Hz, 2H), 4.48-4.64 (m, 1H).

MS(ESI)(Pos)m/z; 324 (M+Na)$^+$ $[α]_D^{25}$=+6.4° (CHCl$_3$, c=1.0)

EXAMPLE 2

Synthesis of (1R,2S,3R,5R,6R)-2-amino-3-(3,4-dichlorobenzylsulfanyl)-6-fluoro-bicyclo[3.1.0]hexane-2,6-dicarboxylic acid diethyl ester, and of (1R,2S,3R,5R,6R)-2-amino-3-(3,4-dichlorobenzylsulfanyl)-6-fluoro-bicyclo[3.1.0]hexane-2,6-dicarboxylic acid (1) 0.36 mL of trifluoromethane sulfonic acid anhydride dissolved in 1.2 mL of dichloromethane was added dropwise to 364 mg of (1R,2R,3S,5R,6R)-2-azido-6-fluoro-3-hydroxy-bicyclo[3.1.0]hexane-2,6-dicarboxylic acid diethyl ester dissolved in 6.1 mL of dichloromethane and 0.21 mL of pyridine at −77° C. to −69° C., under a nitrogen atmosphere. The mixture was stirred for 30 minutes at −77° C., and further stirred for 30 minutes at ice-cooling. 30 mL of diethyl ether was added thereto, and after the solids were filtered off, the filtrate was concentrated under reduced pressure. The residue was purified by column chromatography (silica gel: Wako gel C200, eluent: hexane-ethyl acetate=5:1), thereby yielding 487 mg of (1R,2R,3S,5R,6R)-2-azido-6-fluoro-3-trifluoromethanesulfonyloxy-bicyclo[3.1.0]hexane-2,6-dicarboxylic acid diethyl ester.

$^1$H-NMR(200 MHz, CDCl$_3$)δ(ppm); 1.36 (t, J=7.0 Hz, 3H), 1.39 (t, J=7.5 Hz, 3H), 2.26-2.63 (m, 3H), 2.91-3.10 (m, 1H), 4.25-4.45 (m, 4H), 5.57 (dd, J=9.0, 2.9 Hz, 1H).

MS(ESI)(Pos)m/z; 456 (M+Na)$^+$ $[α]_D^{26}$=−41.4° (CHCl$_3$, c=1.1)

(2) 2.59 g of 3,4-dichlorobenzylmercaptan was addd to 308 mg of sodium dissolved in 18 mL of ethanol, and the mixture was stirred for 5 minutes at room temperature under a nitrogen atmosphere, and then concentrated under reduced pressure. 64 mL of dimethylsulfoxide was added to the residue, and after 3.23 g of (1R,2R,3S,5R,6R)-2-azido-6-fluoro-3-trifluoromethanesulfonyloxy-bicyclo[3.1.0]hexane-2,6-dicarboxylic acid diethyl ester dissolved in 6.4 mL of dimethylsulfoxide was added thereto, the mixture was stirred for 10 minutes at room temperature. 250 mL of diethyl ether was added thereto, and the upper and lower layers were separated. The lower layer was extracted twice with diethyl ether. The organic layers were combined, washed with cold 1N hydrochloric acid and with a saturated aqueous solution of sodium chloride, and then dried over anhydrous sodium sulfate. The desiccant was filtered off, and the filtrate was concentrated under reduced pressure. The residue was purified by column chromatography (silica gel: Wako gel C200 (made by Wako Pure Chemical Industries Ltd.), eluent: hexane-ethyl acetate=10:1 to 5:1), thereby yielding 3.35 g of (1R,2S,3R,5R,6R)-2-azido-3-(3,4-dichlorobenzylsulfanyl)-6-fluoro-bicyclo[3.1.0]hexane-2,6-dicarboxylic acid diethyl ester.

$^1$H-NMR(200 MHz, CDCl$_3$)δ(ppm); 1.34 (t, J=7.0 Hz, 3H), 1.38 (t, J=7.0 Hz, 3H), 2.20-2.49 (m, 4H), 2.99-3.13 (m, 1H), 3.68 (d, J=13.6 Hz, 1H), 3.84 (d, J=13.6 Hz, 1H), 4.22-4.51 (m, 4H), 7.16 (dd, J=8.1, 2.0 Hz, 1H), 7.34-7.46 (m, 2H).

MS(ESI)(Pos)m/z; 498 (M+Na)$^+$ $[α]_D^{24}$=+129.9° (CHCl$_3$, c=0.5)

(3) 7.7 mL of a solution of 1M trimethylphosphine/tetrahydrofuran was added to 3.35 g of (1R,2S,3R,5R,6R)-2-azido-3-(3,4-dichlorobenzylsulfanyl)-6-fluoro-bicyclo[3.1.0]hexane-2,6-dicarboxylic acid diethyl ester dissolved in 100 mL of tetrahydrofuran and 10 mL of water, and the mixture was stirred for 1 hour at room temperature. The mixture was diluted with 200 mL of diethyl ether, and after 50 mL of a saturated aqueous solution of sodium hydrogen carbonate was added thereto, the mixture was stirred for 1.5 hours at room temperature. After separation, the organic layers were washed with a saturated aqueous solution of sodium chloride and then dried over anhydrous sodium sulfate. The desiccant was filtered off, and the filtrate was concentrated under reduced pressure. The residue was diluted with chloroform, and then silica gel (Wako gel C200 (made by Wako Pharmaceutical Industries Ltd.)) was added thereto. The mixture was concentrated under reduced pressure, left to stand for 18 hours at room temperature, and then purified by column chromatography (silica gel: Wako gel C200 (made by Wako Pure Chemical Industries Ltd.), eluent: hexane-ethyl acetate=2:1), thereby yielding 2.78 g of (1R,2S,3R,5R,6R)-2-amino-3-(3,4-dichlorobenzylsulfanyl)-6-fluoro-bicyclo[3.1.0]hexane-2,6-dicarboxylic acid diethyl ester.

(4) 12 mg of lithium hydroxide hydrate was added to 41 mg of (1R,2S,3R,5R,6R)-2-amino-3-(3,4-dichlorobenzylsulfanyl-6-fluoro-bicyclo[3.1.0]hexane-2,6-dicarboxylic acid diethyl ester dissolved in 0.8 mL of tetrahydrofuran and 0.4 mL of water, and the mixture was stirred for 5.5 days at room temperature. The mixture was adjusted to pH=3 with 1N hydrochloric acid in an ice bath. After 30 mL of water was added thereto, the mixture was stirred for 1 hour at room temperature and then purified by ion exchange resin (AG 50W-X8 Resin (H form), eluent: water, a 40% aqueous solution of tetrahydrofuran, a 10% aqueous solution of pyridine), and the obtained solids were further washed with tetrahydrofuran, thereby yielding 25 mg of (1R,2S,3R,5R,6R)-2-amino-3-(3,4-dichlorobenzylsulfanyl)-6-fluoro-bicyclo[3.1.0]hexane-2,6-dicarboxylic acid.

EXAMPLE 3

Synthesis of (1R,2S,3R,5R,6R)-2-amino-3-(3,4-dichlorobenzylsulfinyl)-6-fluoro-bicyclo[3.1.0]hexane-2,6-dicarboxylic acid diethyl ester, and of (1R,2S,3R,5R,6R)-2-amino-3-(3,4-dichlorobenzylsulfinyl)-6-fluoro-bicyclo[3.1.0]hexane-2,6-dicarboxylic acid (1) 32 mg of 3-chloroperbenzoic acid was added to 73 mg of (1R,2S,3R,5R,6R)-2-azido-3-(3,4-dichlorobenzylsulfanyl)-6-fluoro-bicyclo[3.1.0]hexane-2,6-dicarboxylic acid diethyl ester dissolved in 1.46 mL of dichloromethane and the mixture was stirred for 1 hour in a dry ice-acetone bath. The mixture was stirred for 3.5 hours in an ice bath, and further stirred for 11 hours at room temperature. 15 mg of 3-chloroperbenzoic acid was further added thereto, and the mixture was stirred for 1 hour in a dry ice-acetone bath, and then stirred for 4 hours in an ice bath. The reaction solution was washed with a saturated aqueous solution of sodium hydrogen carbonate and with a saturated aqueous solution of sodium chloride, and then dried over anhydrous sodium sulfate. The desiccant was filtered off, and the filtrate was concentrated under reduced pressure. The residue was purified by column chromatography (silica gel: Wako gel C200 (made by Wako Pure Chemical Industries Ltd.), eluent: hexane-ethyl acetate=4:1 to 2:1), thereby yielding 63 mg of (1R,2S,3R,5R,6R)-2-azido-3-(3,4-dichlorobenzylsulfinyl)-6-fluoro-bicyclo[3.1.0]hexane-2,6-dicarboxylic acid diethyl ester and 12 mg of (1R,2S,3R,5R,6R)-2-azido-3-(3,4-dichlorobenzylsulfonyl-6-fluoro-bicyclo[3.1.0]hexane-2,6-dicarboxylic acid diethyl ester.

(1R,2S,3R,5R,6R)-2-azido-3-(3,4-dichlorobenzylsulfinyl)-6-fluoro-bicyclo[3.1.0]hexane-2,6-dicarboxylic acid diethyl ester $^1$H-NMR(200 MHz, CDCl$_3$)δ(ppm); 1.36 (t, J=7.0 Hz, 3H), 1.38 (t, J=7.0 Hz, 3H), 2.33 (dd, J=14.1, 8.4 Hz, 1H), 2.43-2.61 (m, 2H), 2.80-2.97 (m, 1H), 3.11-3.24 (m, 1H), 3.79 (d, J=13.2 Hz, 1H), 4.09 (d, J=13.2 Hz, 1H), 4.25-4.43 (m, 4H), 7.17 (dd, J=8.4, 2.2 Hz, 1H), 7.40-7.50 (m, 2H).
MS(ESI)(Pos) m/z; 514 (M+Na)$^+$
$[α]_D^{28}$=+36.0° (CHCl$_3$, c=0.5)

(1R,2S,3R,5R,6R)-2-azido-3-(3,4-dichlorobenzylsulfonyl)-6-fluoro-bicyclo[3.1.0]hexane-2,6-dicarboxylic acid diethyl ester $^1$H-NMR(200 MHz, CDCl$_3$)δ(ppm); 1.36 (t, J=7.0 Hz, 3H), 1.39 (t, J=7.0 Hz, 3H), 2.33-2.58 (m, 3H), 2.86-3.05 (m, 1H), 3.53 (dd, J=11.2, 8.1 Hz, 1H), 4.24-4.46 (m, 6H), 7.28 (dd, J=8.4, 2.2 Hz, 1H), 7.44-7.56 (m, 2H).
MS(ESI)(Pos)m/z; 530 (M+Na)$^+$
$[α]_D^{29}$=+7.9° (CHCl$_3$, c=0.7)

(2) By means of the same method as Example 2 (3), 41 mg of (1R,2S,3R,5R,6R)-2-amino-3-(3,4-dichlorobenzylsulfinyl)-6-fluoro-bicyclo[3.1.0]hexane-2,6-dicarboxylic acid diethyl ester was yielded from 61 mg of (1R,2S,3R,5R,6R)-2-azido-3-(3,4-dichlorobenzylsulfinyl-6-fluoro-bicyclo[3.1.0]hexane-2,6-dicarboxylic acid diethyl ester.

(3) By means of the same method as Example 2 (4), 17 mg of (1R,2S,3R,5R,6R)-2-amino-3-(3,4-dichlorobenzylsulfinyl)-6-fluoro-bicyclo[3.1.0]hexane-2,6-dicarboxylic acid was yielded from 38 mg of (1R,2S,3R,5R,6R)-2-amino-3-(3,4-dichlorobenzylsulfinyl-6-fluoro-bicyclo[3.1.0]hexane-2,6-dicarboxylic acid diethyl ester.

EXAMPLE 4

Synthesis of (1R,2S,3R,5R,6R)-2-amino-3-(3,4-dichlorobenzylsulfonyl)-6-fluoro-bicyclo[3.1.0]hexane-2,6-dicarboxylic acid and of (1R,2S,3R,5R,6R)-2-amino-3-(3,4-dichlorobenzylsulfonyl)-6-fluoro-bicyclo[3.1.0]hexane-2,6-dicarboxylic acid By means of the same method as Example 2 (3), 169 mg of (1R,2S,3R,5R,6R)-2-amino-3-(3,4-dichlorobenzylsulfonyl)-6-fluoro-bicyclo[3.1.0]hexane-2,6-dicarboxylic acid diethyl ester was yielded from 190 mg of (1R,2S,3R,5R,6R)-2-azido-3-(3,4-dichlorobenzylsulfonyl)-6-fluoro-bicyclo[3.1.0]hexane-2,6-dicarboxylic acid diethyl ester.

(2) 108 mg of (1R,2S,3R,5R,6R)-2-amino-3-(3,4-dichlorobenzylsulfonyl)-6-fluoro-bicyclo[3.1.0]hexane-2,6-dicarboxylic acid diethyl ester was stirred in 1.08 mL of 60% sulfuric acid (W/V %) for 3 days at 130° C. The reaction solution was ice-cooled and then neutralized in an aqueous solution of 5N sodium hydroxide. The mixture was stirred for 1 hour at room temperature and then purified by ion exchange resin (AG 50W-X8 Resin (H form), eluent: water, a 30% aqueous solution of tetrahydrofuran and a 10% aqueous solution of pyridine), thereby yielding 76 mg of (1R,2S,3R,5R,6R)-2-amino-3-(3,4-dichlorobenzylsulfonyl)-6-fluoro-bicyclo[3.1.0]hexane-2,6-dicarboxylic acid.

EXAMPLE 5

Synthesis of (1R,2R,3R,5R,6R)-2,3-diamino-6-fluoro-bicyclo[3.1.0]hexane-2,6-dicarboxylic acid diethyl ester and of (1R,2R,3R,5R,6R)-2,3-diamino-6-fluoro-bicyclo[3.1.0]hexane-2,6-dicarboxylic acid 56 mg of sodium azide was added to 250 mg of (1R,2R,3S,5R,6R)-2-azido-6-fluoro-3-trifluoromethanesulfonyloxy-bicyclo[3.1.0]hexane-2,6-dicarboxylic acid diethyl ester dissolved in 5 mL of N,N-dimethylformamide, and the mixture was stirred for 30 minutes at room temperature. After 100 mL of diethyl ether was added to the reaction solution, this ether solution was washed four times with water and then dried over anhydrous sodium sulfate. The desiccant was filtered off, and the filtrate was concentrated under reduced pressure The residue was purified by column chromatography (silica gel: Wako gel C200 (made by Wako Pure Chemical Industries Ltd.), eluent: hexane-ethyl acetate=10:1), thereby yielding 175 mg of (1R,2R,3R,5R,6R)-2,3-diazido-6-fluoro-bicyclo[3.1.0]hexane-2,6-dicarboxylic acid diethyl ester.

$^1$H-NMR(200 MHz, CDCl$_3$)δ(ppm); 1.34 (t, J=7.0 Hz, 3H), 1.40 (t, J=7.0 Hz, 3H), 2.25-2.57 (m, 4H), 3.94-4.04 (m, 1H), 4.24-4.45 (m, 4H).
MS(ESI)(POS)m/z; 349 (M+Na)$^+$
$[α]_D^{26}$=+32.7° (CHCl$_3$, c=0.59)

25 mg of 10% palladium carbon was added to 170 mg of (1R,2R,3R,5R,6R)-2,3-diazido-6-fluoro-bicyclo[3.1.0]hexane-2,6-dicarboxylic acid diethyl ester dissolved in a mixture of 15 mL of acetic acid and 5 mL of water, and the mixture was stirred for 24 hours at room temperature under a hydrogen atmosphere. After celite filturation, the solvent was distilled off at 50° C. under reduced pressure, thereby yielding 42 mg of (1R,2R,3R,5R,6R)-2,3-diamino-6-fluoro-bicyclo[3.1.0]hexane-2,6-dicarboxylic acid diethyl ester.

(3) By means of the same method as Example 2 (4), 14 mg of (1R,2R,3R,5R,6R)-2,3-diamino-6-fluoro-bicyclo[3.1.0]hexane-2,6-dicarboxylic acid was yielded from 42 mg of (1R,2R,3R,5R,6R)-2,3-diamino-6-fluoro-bicyclo[3.1.0]hexane-2,6-dicarboxylic acid 6-ethyl ester.

EXAMPLE 6

Synthesis of (1R,2R,3R,5R,6R)-2-amino-3-(3,4-dichlorobenzylamino)-6-fluoro-bicyclo[3.1.0]hexane-2,6-dicarboxylic acid diethyl ester and of (1R,2R,3R,5R,6R)-2-amino-3-(3,4-dichlorobenzylamino)-6-fluoro-bicyclo[3.1.0]hexane-2,6-dicarboxylic acid (1) 0.89 mL of a solution of 1M trimethylphosphine/tetrahydrofuran was added to 245 mg of (1R,2R,3S,5R,6R)-2-azido-6-fluoro-3-hydroxy-bicyclo[3.1.0]hexane-2,6-dicarboxylic acid diethyl ester dissolved in 7.0 mL of tetrahydrofuran and 0.7 mL of water, and the mixture was stirred for 12 hours at room temperature. After the mixture was diluted with 14 mL of diethyl ether, a saturated aqueous solution of sodium hydrogen carbonate was added thereto, and the mixture was stirred for 1 hour at room temperature. After separation, the aqueous layer was extracted twice with chloroform. The organic layers were combined, washed with a saturated aqueous solution of sodium chloride and then dried over anhydrous sodium sulfate. The desiccant was filtered off, and the filtrate was concentrated under reduced pressure The residue was purified by column chromatography (silica gel: Wako gel C200 (made by Wako Pure Chemical Industries Ltd.), eluent: chloroform-ethanol=50:1), thereby yielding 163 mg of (1R,2R,3S,5R,6R)-2-amino-6-fluoro-3-hydroxy-bicyclo[3.1.0]hexane-2,6-dicarboxylic acid diethyl ester.

$^1$H-NMR(200 MHz, CDCl$_3$)δ(ppm); 1.32 (t, J=7.3 Hz, 6H), 2.07-2.23 (m, 2H), 2.41 (dd, J=8.1, 3.3 Hz, 1H), 2.71-2.91 (m, 1H), 4.10-4.41 (m, 5H).

MS(ESI)(Pos) m/z; 276 (M+H)$^+$ $[α]_D^{25}$=+2.8° (CHCl$_3$, c=1.5)

(2) 0.8 mL of a saturated aqueous solution of sodium hydrogen carbonate and 152 mg of di-t-butyldicarbonate were added to 160 mg of (1R,2R,3S,5R,6R)-2-amino-6-fluoro-3-hydroxy-bicyclo[3.1.0]hexane-2,6-dicarboxylic acid diethyl ester dissolved in 0.8 mL of tetrahydrofuran, and the mixture was stirred for 4 hours, at room temperature. The reaction solution was extracted twice with ethyl acetate. The organic layers were combined, washed with a saturated aqueous solution of sodium chloride and then dried over anhydrous sodium sulfate. The desiccant was filtered off, and the filtrate was concentrated under reduced pressure. The residue was purified by column chromatography (silica gel: Wako gel C200 (made by Wako Pure Chemical Industries Ltd.), eluent: hexane-ethyl acetate=2:1), thereby yielding 214 mg of (1R,2R,3S,5R,6R)-2-butoxycarbonylamino-6-fluoro-3-hydroxy-bicyclo[3.1.0]hexane-2,6-dicarboxylic acid diethyl ester.

$^1$H-NMR(200 MHz, CDCl$_3$)δ(ppm); 1.29 (t, J=7.0 Hz, 3H), 1.30 (t, J=7.0 Hz, 3H), 1.44 (s, 9H), 2.20-2.48 (m, 3H), 2.77-2.98 (m, 2H), 4.07-4.48 (m, 5H), 5.57 (s, 1H).

MS(ESI)(Pos)m/z; 398 (M+Na)$^+$ $[α]_D^{22}$=−14.0 (CHCl$_3$, c=0.9)

(3) By means of the same method as Example 2 (1), 1.65 g of (1R,2R,3S,5R,6R)-2-butoxycarbonylamino-6-fluoro-3-trifluoromethanesulfonyloxy-bicyclo[3.1.0]hexane-2,6-dicarboxylic acid diethyl ester was yielded from 1.47 g of (1R,2R,3S,5R,6R)-2-butoxycarbonylamino-6-fluoro-3-hydroxy-bicyclo[3.1.0]hexane-2,6-dicarboxylic acid diethyl ester.

$^1$H-NMR(200 MHz, CDCl$_3$)δ(ppm); 1.25-1.41 (m, 6H), 1.44 (s, 9H), 2.13-2.26 (m, 1H), 2.40-2.57 (m, 2H), 2.97-3.20 (m, 1H), 4.14-4.47 (m, 4H), 5.32 (s, 1H), 5.99 (d, J=8.4 Hz, 1H).

MS(ESI)(Nega)m/z; 506 (M−H)$^−$ $[α]_D^{28}$=+79.8° (CHCl$_3$, c=0.5)

(4) 313 mg of sodium azide was added to 1.63 g of (1R,2R,3S,5R,6R)-2-t-butoxycarbonylamino-6-fluoro-3-trifluoromethanesulfonyloxy-bicyclo[3.1.0]hexane-2,6-dicarboxylic acid diethyl ester dissolved in 16.3 mL of N,N-dimethylformamide, and the mixture was stirred for 1 hour at room temperature, and then for 20 hours at 35° C. After 104 mg of sodium azide was further added thereto, the mixture was stirred for 18 hours at 35° C. The mixture was diluted with 50 mL of diethyl ether, and then washed twice with water and with a saturated aqueous solution of sodium chloride. The organic layers were dried over anhydrous sodium sulfate. The desiccant was filtered off, and the filtrate was concentrated under reduced pressure. The residue was purified by column chromatography (silica gel: Wako gel C200 (made by Wako Pure Chemical Industries Ltd.), eluent: hexane-ethyl acetate=5:1), thereby yielding 775 mg of (1R,2R,3R,5R,6R)-3-azido-2-t-butoxycarbonylamino-6-fluoro-bicyclo[3.1.0]hexane-2,6-dicarboxylic acid diethyl ester.

$^1$H-NMR(200 MHz, CDCl$_3$)δ(ppm); 1.29 (t, J=7.0 Hz, 3H), 1.33 (t, J=7.0 Hz, 3H), 1.45 (s, 9H), 2.21-2.56 (m, 3H), 2.92 (dd, J=7.7, 2.4 Hz, 1H), 3.78-3.88 (m, 1H), 4.17-4.41 (m, 4H), 5.01 (s, 1H).

MS(ESI)(Pos) m/z; 423 (M+Na)

$[α]D^{26}$=+0.79° (CHCl$_3$, c=1.4)

(5) By means of the same method as Example. 6 (1), 553 mg of (1R,2R,3R,5R,6R)-3-amino-2-t-butoxycarbonylamino-6-fluoro-bicyclo[3.1.0]hexane-2,6-dicarboxylic acid diethyl ester was yielded from 725 mg of (1R,2R,3R,5R,6R)-3-azido-2-t-butoxycarbonylamino-6-fluoro-bicyclo[3.1.0]hexane-2,6-dicarboxylic acid diethyl ester.

$^1$H-NMR(200 MHz, CDCl$_3$)δ(ppm); 1.30 (t, J=7.0 Hz, 3H), 1.32 (t, J=7.0 Hz, 3H), 1.44 (s, 9H), 2.06-2.27 (m, 2H), 2.40-2.55 (m, 1H), 2.61-2.72 (m, 1H), 3.28-3.47 (m, 1H), 4.17-4.41 (m, 4H), 5.05 (s, 1H).

MS(ESI)(Pos) m/z; 397 (M+Na)$^+$ $[α]_D^{27}$=−14.2° (CHCl$_3$, c=1.4)

(6) 42 μL of pyridine and 123 mg of 3,4-dichlorobenzylbromide were added to 175 mg of (1R,2R,3R,5R,6R)-3-amino-2-t-butoxycarbonylamino-6-fluoro-bicyclo[3.1.0]hexane-2,6-dicarboxylic acid diethyl ester dissolved in 0.88 mL of chloroform at ice-cooling, and then the mixture was stirred for 3 days at room temperature. A saturated aqueous solution of sodium chloride was added thereto, and the mixture was extracted five times with chloroform. The organic layers were combined and then dried over anhydrous sodium sulfate. The desiccant was filtered off, and the filtrate was concentrated under reduced pressure. The residue was purified by column chromatography (silica gel: Wako gel C200 (made by Wako Pure Chemical Industries Ltd.), eluent: chloroform-ethanol=100:1 to 50:1, followed by hexane-ethyl acetate=5:1), thereby yielding 98 mg of (1R,2R,3R,5R,6R)-2-t-butoxycarbonylamino-3-(3,4-dichlorobenzylamino)-6-fluoro-bicyclo[3.1.0]hexane-2,6-dicarboxylic acid diethyl ester.

$^1$H-NMR(200 MHz, CDCl$_3$)δ(ppm); 1.23-1.34 (m, 6H), 1.44 (s, 9H), 2.03-2.26 (m, 2H), 2.43 (dd, J=13.0, 7.3 Hz, 1H), 2.83-2.93 (m, 1H), 3.02-3.15 (m, 1H), 3.71 (d, J=13.2 Hz, 1H), 3.80 (d, J=13.2 Hz, 1H), 4.12-4.39 (m, 4H), 4.82 (s, 1H), 7.11 (dd, J=8.1, 2.0 Hz, 1H), 7.33-7.45 (m, 2H).

MS(ESI)(Nega)m/z; 531 (M−H)$^−$ $[α]_D^{27}$=−15.1° (CHCl$_3$, c=0.5)

(7) 2.8 mL of a solution of 4N hydrogen chloride/ethyl acetate was added to 28 mg of (1R,2R,3R,5R,6R)-2-t-butoxycarbonylamino-3-(3,4-dichlorobenzylamino)-6-fluoro-bicyclo[3.1.0]hexane-2,6-dicarboxylic acid diethyl ester, and the mixture was stirred for 6 hours at ice-cooling and further stirred for 18 hours at room temperature. The reaction solution was ice-cooled and then neutralized with a saturated aqueous solution of sodium hydrogen carbonate, followed by separation. The aqueous layer was extracted with ethyl acetate. The organic layers were combined, washed with a saturated aqueous solution of sodium chloride and then dried over anhydrous sodium sulfate. The desiccant was filtered off, and the filtrate was concentrated under reduced pressure, thereby yielding 21 mg of (1R,2R,3R,5R,6R)-2-amino-3-(3,4-dichlorobenzylamino)-6-fluoro-bicyclo[3.1.0]hexane-2,6-dicarboxylic acid diethyl ester.

(8) By means of the same method as Example 2 (4), 17 mg of (1R,2R,3R,5R,6R)-2-amino-3-(3,4-dichlorobenzylamino)-6-fluoro-bicyclo[3.1.0]hexane-2,6-dicarboxylic acid was yielded from 28 mg of (1R,2R,3R,5R,6R)-2-amino-3-(3,4-dichlorobenzylamino)-6-fluoro-bicyclo[3.1.0]hexane-2,6-dicarboxylic acid diethyl ester.

EXAMPLE 7

Synthesis of (1R,2R,3R,5R,6R)-2-amino-3-[N,N-(3,4-dichlorobenzyl) methylamino]-6-fluoro-bicyclo[3.1.0]hexane-2,6-dicarboxylic acid diethyl ester and of (1R,2R,3R,5R,6R)-2-amino-3-[N,N-(3,4-dichlorobenzyl)methylamino]-6-fluorobicyclo[3.1.0]hexane-2,6-dicarboxylic acid (1) 71 mg of potassium carbonate and 64 µL of methyl iodide were added to 136 mg of (1R,2R,3R,5R,6R)-2-t-butoxycarbonylamino-3-(3,4-dichlorobenzylamino)-6-fluoro-bicyclo[3.1.0]hexane-2,6-dicarboxylic acid diethyl ester dissolved in 1.36 mL of N,N-dimethylformamide, and the mixture was stirred for 3 days at room temperature. A saturated aqueous solution of sodium thiosulfate was added thereto, and the mixture was extracted twice with ethyl acetate. The organic layers were combined, washed with a saturated aqueous solution of sodium chloride, and then dried over anhydrous sodium sulfate. The desiccant was filtered off, and the filtrate was concentrated under reduced pressure The residue was purified by column chromatography (silica gel: Wako gel C200 (made by Wako Pure Chemical Industries Ltd.), eluent: hexane-ethyl acetate=5:1), thereby yielding 126 mg of (1R,2R,3R,5R,6R)-2-t-butoxycarbonylamino-3-[N,N-(3,4-dichlorobenzyl)methylamino]-6-fluoro-bicyclo[3.1.0]hexane-2,6-dicarboxylic acid diethyl ester.

$^1$H-NMR(200 MHz, CDCl$_3$)δ(ppm); 1.28 (t, J=7.0 Hz, 3H), 1.29 (t, J=7.0 Hz, 3H), 1.43 (s, 9H), 2.11 (s, 3H), 2.16-2.58 (m, 3H), 2.80-3.07 (m, 2H), 3.29 (d, J=13.6 Hz, 1H), 3.78 (d, J=13.6 Hz, 1H), 4.05-4.43 (m, 4H), 4.86 (s, 1H), 7.08 (dd, J=8.4, 1.8 Hz, 1H), 7.31-7.41 (m, 2H).

MS(ESI)(Pos)m/z; 547 (M+H)$^+$ $[α]_D^{25}$=−51.9° (CHCl$_3$, c=0.5)

(2) By means of the same method as Example 6 (7), 96 mg of (1R,2R,3R,5R,6R)-2-amino-3-[N,N-(3,4-dichlorobenzyl)methylamino]-6-fluoro-bicyclo[3.1.0]hexane-2,6-dicarboxylic acid diethyl ester was yielded from 124 mg of (1R,2R,3R,5R,6R)-2-t-butoxycarbonylamino-3-[N,N-(3,4-dichlorobenzyl)methylamino]-6-fluoro-bicyclo[3.1.0]hexane-2,6-dicarboxylic acid diethyl ester.

(3) By means of the same method as Example 2 (4), 62 mg of (1R,2R,3R,5R,6R)-2-amino-3-[N,N-(3,4-dichlorobenzyl)methylamino]-6-fluoro-bicyclo[3.1.0]hexane-2,6-dicarboxylic acid was yielded from 94 mg of (1R,2R,3R,5R,6R)-2-amino-3-[(3,4-dichlorobenzyl)methylamino]-6-fluoro-bicyclo[3.1.0]hexane-2,6-dicarboxylic acid diethyl ester.

EXAMPLE 8

Synthesis of (1R,2R,3R,5R,6R)-2-amino-3-(3,4-dichlorobenzoylamino)-6-fluoro-bicyclo[3.1.0]hexane-2,6-dicarboxylic acid diethyl ester and of (1R,2R,3R,5R,6R)-2-amino-3-(3,4-dichlorobenzoylamino)-6-fluoro-bicyclo[3.1.0]hexane-2,6-dicarboxylic acid (1) 7.3 µL of pyridine and 14 mg of 3,4-dichlorobenzoyl chloride were added to 17 mg of (1R,2R,3R,5R,6R)-3-amino-2-t-butoxycarbonylamino-6-fluoro-bicyclo[3.1.0]hexane-2,6-dicarboxylic acid diethyl ester dissolved in 0.17 mL of chloroform, and the mixture was stirred for 3 hours at room temperature. The reaction solution was concentrated under reduced pressure The residue was purified by column chromatography (silica gel: Wako gel C200 (made by Wako Pure Chemical Industries Ltd.), eluent: chloroform-ethanol=100:1), thereby yielding 21 mg of (1R,2R,3R,5R,6R)-2-t-butoxycarbonylamino-3-(3,4-dichlorobenzoylamino)-6-fluoro-bicyclo[3.1.0]hexane-2,6-dicarboxylic acid diethyl ester.

$^1$H-NMR(200 MHz, CDCl$_3$)δ(ppm); 1.19 (t, J=7.0 Hz, 3H), 1.31 (t, J=7.3 Hz, 3H), 1.41 (s, 9H), 2.21-2.64 (m, 3H), 2.82-2.91 (m, 1H), 4.07-4.37 (m, 4H), 4.58-4.75 (m, 1H), 6.20 (s, 1H), 6.39-6.50 (m, 1H), 7.46-7.57 (m, 2H), 7.80-7.85 (m, 1H).

MS(ESI)(Nega)m/z; 545 (M−H)$^-$ $[α]_D^3$=+12.1 (CDCl$_3$, c=0.9)

(2) By means of the same method as Example 6 (7), 85 mg of (1R,2R,3R,5R,6R)-2-amino-3-(3,4-dichlorobenzoylamino)-6-fluoro-bicyclo[3.1.0]hexane-2,6-dicarboxylic acid diethyl ester was yielded from 107 mg of (1R,2R,3R,5R,6R)-2-t-butoxycarbonylamino-3-(3,4-dichlorobenzoylamino)-6-fluoro-bicyclo[3.1.0]hexane-2,6-dicarboxylic acid diethyl ester.

(3) By means of the same method as Example 2 (4), 24 mg of (1R,2R,3R,5R,6R)-2-amino-3-(3,4-dichlorobenzoylamino)-6-fluoro-bicyclo[3.1.0]hexane-2,6-dicarboxylic acid was yielded from 48 mg of (1R,2R,3R,5R,6R)-2-amino-3-(3,4-dichlorobenzoylamino)-6-fluoro-bicyclo[3.1.0]hexane-2,6-dicarboxylic acid diethyl ester.

EXAMPLE 9

Synthesis of (1R,2R,3R,5R,6R)-2-amino-3-(3,4-dichlorobenzoyloxy)-6-fluoro-bicyclo[3.1.0]hexane-2,6-dicarboxylic acid 2-benzyl ester 6-ethyl ester and of (1R,2R,3R,5R,6R)-2-amino-3-(3,4-dichlorobenzoyloxy)-6-fluoro-bicyclo[3.1.0]hexane-2,6-dicarboxylic acid (1) 234 mg of 3,4-dichlorobenzoyl chloride was added to 202 mg of (1R,2R,3R,5R,6R)-2-azido-6-fluoro-3-hydroxy-bicyclo[3.1.0]hexane-2,6-dicarboxylic acid 2-benzyl ester 6-ethyl ester dissolved in 3.7 mL of pyridine, and the mixture was stirred for 28 hours at room temperature, under a nitrogen atmosphere. After 100 mL of ethyl acetate was added to the reaction solution, this ethyl acetate solution was washed with a saturated aqueous solution of copper sulfate and with water, and then dried over anhydrous sodium sulfate. The desiccant was filtered off, and the filtrate was concentrated under reduced pressure. The residue was purified by column chromatography (silica gel: Wako gel C200, eluent: hexane-ethyl acetate=10:1), thereby yielding 298 mg of (1R,2R,3R,5R,6R)-2-azido-3-(3,4-dichlorobenzoyloxy)-6-fluoro-bicyclo[3.1.0]hexane-2,6-dicarboxylic acid 2-benzyl ester 6-ethyl ester.

$^1$H-NMR(200 MHz, CDCl$_3$)δ(ppm); 1.35 (t, J=7.3 Hz, 3H), 2.35-2.55 (m, 3H), 2.77-2.87 (m, 1H), 4.31 (q, J=7.3 Hz, 2H), 5.24-5.46 (m, 3H), 7.28-7.60 (m, 6H), 7.90-8.20 (m, 2H).

MS(ESI)(Pos)m/z; 558 (M+Na)$^+$ (2) By means of the same method as Example 2 (3), 218 mg of (1R,2R,3R,5R,6R)-2-amino-3-(3,4-dichlorobenzoyloxy)-6-fluoro-bicyclo[3.1.0]hexane-2,6-dicarboxylic acid 2-benzyl ester 6-ethyl ester was yielded from 298 mg of (1R,2R,3R,5R,6R)-2-azido-3-(3,4-dichlorobenzoyloxy)-6-fluoro-bicyclo[3.1.0]hexane-2,6-dicarboxylic acid 2-benzyl ester 6-ethyl ester.

(3) 15 mg of 5% palladium carbon was added to 218 mg of (1R,2R,3R,5R,6R)-2-amino-3-(3,4-dichlorobenzoyloxy)-6-fluoro-bicyclo[3.1.0]hexane-2,6-dicarboxylic acid 2-benzyl ester 6-diethyl ester dissolved in 10 mL of ethanol, and the mixture was stirred for 50 minutes at room temperature, under a hydrogen atmosphere. After the palladium carbon was filtered through celite, the filtrate was concentrated under reduced pressure, and the obtained solids were dissolved in a mixture of 2 mL of tetrahydrofuran and 1 mL of water. 10 mg of lithium hydroxide monohydrate was added to this solution, and the mixture was stirred for 30 minutes at ice-cooling. After 0.5 mL of 1N hydrochloric acid was added thereto at ice-cooling, the mixture was diluted with 50 mL of water and then purified by ion exchange resin (AG 50W-X8 Resin (H form), eluent: water, an aqueous solution of 40% tetrahydrofuran and an aqueous solution of 10% pyridine), thereby yielding 25 mg of (1R,2R,3R,5R,6R)-2-amino-3-(3,4-dichlorobenzoyloxy)-6-fluoro-bicyclo[3.1.0]hexane-2,6-dicarboxylic acid.

EXAMPLE 10

Synthesis of (1R,2S,3R,5R,6R)-2-amino-3-(3,4-dichlorobenzylsulfanyl)-6-fluoro-bicyclo[3.1.0]hexane-2,6-dicarboxylic acid 6-benzyl ester (1) 19 μL of thionyl chloride was added to 26 mg of (1R,2S,3R,5R,6R)-2-amino-3-(3,4-dichlorobenzylsulfanyl)-6-fluoro-bicyclo[3.1.0]hexane-2,6-dicarboxylic acid suspended in 0.3 mL of benzyl alcohol at ice-cooling, and then the mixture was stirred for 3.5 hours at 50° C. After standing to cool, the reaction solution was concentrated under reduced pressure, and the residue was purified by reverse phase column chromatography (Wako gel 50C18 (Wako Pharmaceutical Industries Ltd.), eluent: water to an aqueous 70% solution of acetonitrile), thereby yielding 5 mg of (1R,2S,3R,5R,6R)-2-amino-3-(3,4-dichlorobenzylsulfanyl)-6-fluoro-bicyclo[3.1.0]hexane-2,6-dicarboxylic acid 6-benzyl ester. 2.19-2.43 (3H, m), 2.47-2.63 (1H, m), 2.96-3.12 (1H, m), 3.75 (1H, d, J=13.2 Hz), 3.81 (1H, d, J=13.2 Hz), 5.22 (2H, s), 7.23-7.54 (8H, m)

MS(ESI)(Nega) 482 (M−H)$^-$

EXAMPLE 11

Synthesis of (1R,2S,3R,5R,6R)-2-amino-3-(3,4-dichlorobenzylsulfanyl)-6-fluoro-bicyclo[3.1.0]hexane-2,6-dicarboxylic acid 2-ethyl ester 17 mg of lithium hydroxide monohydrate was added to 150 mg of (1R,2S,3R,5R,6R)-2-amino-3-(3,4-dichlorobenzylsulfanyl)-6-fluoro-bicyclo[3.1.0]hexane-2,6-dicarboxylic acid diethyl ester dissolved in a mixture of 3.5 mL tetrahydrofuran and 1.7 mL of water, and the mixture was stirred for 30 minutes at ice-cooling. The mixture was acidified to pH 2 with 1N hydrochloric acid, diluted with 30 mL of water, and then stirred for 30 minutes at ice-cooling. This diluted solution was purified by ion exchange resin (AG 50W-X8 Resin (H form), eluent: water, a 30% aqueous solution of tetrahydrofuran and a 10% aqueous solution of pyridine), thereby yielding 73 mg of (1R,2S,3R,5R,6R)-2-amino-3-(3,4-dichlorobenzylsulfanyl)-6-fluoro-bicyclo[3.1.0]hexane-2,6-dicarboxylic acid 2-ethyl ester.

The structure and physical data of the compounds described in Examples 2, 3, 4, 5, 6, 7, 8, 9, 10 and 11, as well as those of compounds obtained by means of the same methods are shown in table 1 below.

TABLE 1

The structure and property data of the compounds obtained in the Examples

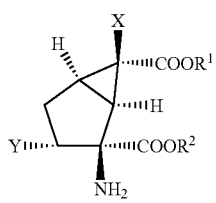

| Compound No. | X | R$^1$ | R$^2$ | Y | NMR | MS | Specific rotatory power | m.p. (° C.) | Example |
|---|---|---|---|---|---|---|---|---|---|
| 1 | F | H | H | S−⟨thiophene⟩−S | (300 MHz, D$_2$O, TMSP) 2.16-2.32(m, 2 H) 2.41-2.50(m, 2 H) 3.06-3.18(m, 1 H) 4.07(s, 2 H) 6.97-7.10(m, 2 H) 7.35-7.43(m, 1 H) | ESI (Nega) 330 (M − H)$^-$ | [α]$_D^{25}$ +38.7 (C = 0.35 1N NaOH) | >230 | 2 |

TABLE 1-continued

The structure and property data of the compounds obtained in the Examples

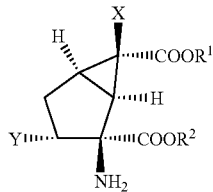

| Compound No. | X | R¹ | R² | Y | NMR | MS | Specific rotatory power | m.p. (° C.) | Example |
|---|---|---|---|---|---|---|---|---|---|
| 2 | F | H | H | ![S-CH2-C6H4-Ph] | (300 MHz, D$_2$O, TMSP) 2.08-2.35(m, 4 H) 2.87-3.00(m, 1 H) 3.78-4.01(m, 2 H) 7.26-7.62(m, 9 H) | ESI (Nega) 400 (M − H)⁻ | $[\alpha]_D^{24}$ +49.3 (C = 0.21 1N NaOH) | >230 | 2 |
| 3 | F | H | H | ![S-CH2-C6H4-OMe] | (300 MHz, D$_2$O, TMSP) 2.16-2.42(m, 4 H) 3.03-3.13(m, 1 H) 3.77-3.87(m, 5 H) 7.00(d, J=8.7 Hz, 2 H) 7.35(d, J=8.7 Hz, 2 H) | ESI (Nega) 354 (M − H)⁻ | $[\alpha]_D^{26}$ +31.0 (C = 0.48 1N NaOH) | >240 | 2 |
| 4 | F | H | H | ![S-CH2-C6H4-F] | (300 MHz, D$_2$O, TMSP) 2.13-2.54(m, 4 H) 2.97-3.19(m, 1 H) 3.84(s, 2 H) 7.03-7.29(m, 2 H) 7.33-7.55(m, 2 H) | ESI (Nega) 342 (M − H)⁻ | $[\alpha]_D^{25}$ +25.4 (C = 0.20 1N NaOH) | >243 | 2 |
| 5 | F | H | H | ![S-CH2-C6H4-tBu] | (300 MHz, D$_2$O, TMSP) 1.31(s, 9 H) 2.20-2.47(m, 4 H) 3.06-3.20(m, 1 H) 3.83(s, 2 H) 7.32-7.40(m, 2 H) 7.46-7.56(m, 2 H) | ESI (Nega) 380 (M − H)⁻ | $[\alpha]_D^{26}$ −1.14 (C = 0.63 1N NaOH) | >271 | 2 |
| 6 | F | H | H | ![S-CH2-C6H4-CF3] | (300 MHz, D$_2$O, TMSP) 2.16-2.47(m, 4 H) 3.04-3.15(m, 1 H) 3.89(d, J=13.2 Hz, 1 H) 3.94(d, J=13.2 Hz, 1 H) 7.50-7.78(m, 4 H) | ESI (Nega) 392 (M − H)⁻ | $[\alpha]_D^{24}$ +38.9 (C = 0.36 1N NaOH) | >271 | 2 |
| 7 | F | H | H | ![S-CH2-naphthyl-Br] | (300 MHz, D$_2$O, TMSP) 2.11-2.43(m, 4 H) 3.23-3.36(m, 1 H) 4.20(d, J=13.4 Hz, 1 H) 4.26(d, J=13.4 Hz, 1 H) 7.53-7.75(m, 3 H) 7.94(t, J=7.8 Hz, 2 H) 8.35(d, J=8.6 Hz, 1 H) | ESI (Nega) 452 (M − H)⁻ | $[\alpha]_D^{27}$ +53.6 (C = 0.20 1N NaOH) | >280 | 2 |
| 8 | H | H | H | ![S-CH2-C6H3-Cl2] | (500 MHz, D$_2$O, TMSP) 1.60(dd, J=3.1, 3.1 Hz) 1.93-1.96(m, 1 H) 2.03-2.05(m, 1 H) 2.15-2.19(m, 2 H) 2.69(dd, J=8.5, 9.7 Hz, 1 H) 3.77(d, J=14.0 Hz, 1 H) 3.81(d, J=14.0 Hz, 1 H) 7.31(dd, J=8.5, 1.8 Hz, 1 H) 7.53(d, J=8.5 Hz, 1 H) 7.58(d, J=1.8 Hz, 1 H) | ESI (Nega) 374 (M − H)⁻ | $[\alpha]_D^{28}$ +22.0 (C = 0.033 1N NaOH) | >289 | 2 |

TABLE 1-continued

The structure and property data of the compounds obtained in the Examples

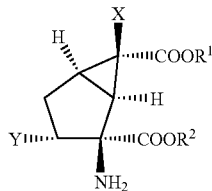

| Compound No. | X | R¹ | R² | Y | NMR | MS | Specific rotatory power | m.p. (° C.) | Example |
|---|---|---|---|---|---|---|---|---|---|
| 9 | F | H | H | S-CH₂-(3,4-dichlorophenyl) | (300 MHz, D₂O, TMSP) 2.17-2.48(m, 4 H) 3.04-3.13(m, 1 H) 3.80(d, J=14.9 Hz, 1 H) 3.85(d, J=14.9 Hz, 1 H) 7.31(d, J=8.1 Hz, 1 H) 7.53(d, J=8.1 Hz, 1 H) 7.59(s, 1 H). | ESI (Nega) 392 (M − H)⁻ | $[\alpha]_D^{30}$ +47.5 (C = 0.41 1N NaOH) | >220 | 2 |
| 10 | F | H | H | S(O)-CH₂-(3,4-dichlorophenyl) | (300 MHz, D₂O, TMSP) 2.16-2.29(m, 1 H) 2.44-2.49(m, 1 H) 2.77-2.88(m, 2 H) 3.44-3.53(m, 1 H) 4.05(d, J=13.1 Hz, 1 H) 4.26(d, J=13.1 Hz, 1 H) 7.29(d, J=8.5 Hz, 1 H) 7.56(s, 1 H) 7.60(d, J=8.5 Hz, 1 H). | ESI (Nega) 408 (M − H)⁻ | $[\alpha]_D^{25}$ +79.7 (C = 0.30 1N NaOH) | >160 | 3 |
| 11 | F | H | H | SO₂-CH₂-(3,4-dichlorophenyl) | (300 MHz, D₂O, TMSP) 2.33-2.45(m, 3 H) 2.82-2.94(m, 1 H) 3.98(dd, J=10.1, 9.48 Hz, 1 H) 4.55(d, J=15.2 Hz, 1 H) 4.60(d, J=15.3 Hz, 1 H) 7.37(d, J=8.5 Hz, 1 H) 7.63(d, J=8.5 Hz, 1 H) 7.64(s, 1 H) | ESI (Nega) 424 (M − H)⁻ | $[\alpha]_D^{28}$ −5.1 (C = 0.72 1N NaOH) | >230 | 4 |
| 12 | F | H | H | S-(3,4-dichlorophenyl) | (300 MHz, D₂O, TMSP) 2.24-2.55(m, 2 H) 2.57-2.94(m, 2 H) 3.51-3.72(m, 1 H) 7.34-7.60(m, 2 H) 7.64-7.80(m, 1 H) | ESI (Nega) 378 (M − H)⁻ | $[\alpha]_D^{25}$ +62.0 (C = 0.26 1N NaOH) | >235 | 2 |
| 13 | F | H | H | S-CH₂-(2,6-difluoro-3-chlorophenyl) | (300 MHz, D₂O, TMSP) 2.09-2.62(m, 4 H) 3.11-3.40(m, 1 H) 3.79-4.11(m, 2 H) 6.87-7.23(m, 1 H) 7.32-7.61(m, 1 H) | ESI (Nega) 394 (M − H)⁻ | $[\alpha]_D^{24}$ +66.9 (C = 0.23 1N NaOH) | >234 | 2 |
| 14 | F | H | H | SPr | (300 MHz, D₂O, TMSP) 0.79-1.00(m, 3 H) 1.20-1.67(m, 4 H) 2.22-0.81(m, 6 H) 3.08-3.30(m, 1 H) | ESI (Nega) 290 (M − H)⁻ | $[\alpha]_D^{24}$ −5.42 (C = 0.12 1N NaOH) | >261 | 2 |
| 15 | F | H | H | S-CH(Me)-phenyl | (300 MHz, D₂O, TMSP) 1.48-1.62(m, 3 H) 1.82-1.94(m, 1 H) 2.05-2.32(m, 2 H) 2.43-2.71(m, 1 H) 2.83-3.03(m, 1 H) 4.04-4.24(m, 1 H) 7.27-7.52(m, 5 H) | ESI (Nega) 338 (M − H)⁻ | — | >307 | 2 |

TABLE 1-continued

The structure and property data of the compounds obtained in the Examples

[Structure: bicyclic compound with X, Y, COOR¹, COOR², NH₂ substituents]

| Compound No. | X | R¹ | R² | Y | NMR | MS | Specific rotatory power | m.p. (° C.) | Example |
|---|---|---|---|---|---|---|---|---|---|
| 16 | F | H | H | bis(4-fluorophenyl)methylthio- (S-CH(C₆H₄F)₂) | (300 MHz, D₂O, TMSP) 2.06-2.60(m, 4 H) 2.91-3.08(m, 1 H) 5.43(s, 1 H) 6.99-7.25(m, 4 H) 7.39-7.65(m, 4 H) | ESI (Nega) 436 (M − H)⁻ | $[\alpha]_D^{24}$ +15.4 (C = 0.36 1N NaOH) | >243 | 2 |
| 17 | F | H | H | NH₂ | (300 MHz, D₂O, TMSP) 2.33-2.79(m, 4 H) 3.77-3.86(m, 1 H) | ESI (Pos) 241 (M + Na)⁺ | $[\alpha]_D^{28}$ −39.3 (C = 0.14 1N NaOH) | >256 | 5 |
| 18 | F | H | H | 3,4-dichlorobenzylamino- (HN-CH₂-C₆H₃Cl₂) | (300 MHz, D₂O, TMSP) 2.31-2.77(m, 4 H) 3.59-3.74(m, 1 H) 4.06(d, J=13.5 Hz, 1 H) 4.15(d, J=13.5 Hz, 1 H) 7.35(d, J=7.8 Hz, 1 H) 7.58-7.64(m, 2 H) | ESI (Nega) 375 (M − H)⁻ | $[\alpha]_D^{27}$ −14.6 (C = 0.29 1N NaOH) | >190 | 6 |
| 19 | F | H | H | N-methyl-3,4-dichlorobenzylamino- (MeN-CH₂-C₆H₃Cl₂) | (300 MHz, D₂O, TMSP) 2.31-2.41(m, 1 H) 2.45-2.53(m, 1 H) 2.64(s, 3 H) 2.73-2.82(m, 2 H) 3.72-3.82(m, 1 H) 4.01(d, J=13.4 Hz, 1 H) 4.27(d, J=13.4 Hz, 1 H) 7.35-7.41(m, 1 H) 7.61-7.69(m, 2 H) | ESI (Nega) 389 (M − H)⁻ | $[\alpha]_D^{24}$ −35.2 (C = 0.51 1N NaOH) | >164 | 7 |
| 20 | F | H | H | 3,4-dichlorobenzamido- (HN-C(O)-C₆H₃Cl₂) | (300 MHz, D₂O, TMSP) 2.33-2.42(m, 2 H) 2.57-2.67(m, 2 H) 4.46-4.55(m, 1 H) 7.58-7.68(m, 2 H) 7.87-7.90(m, 1 H) | ESI (Nega) 389 (M − H)⁻ | $[\alpha]_D^{28}$ +6.0 (C = 0.34 1N NaOH) | >210 | 8 |
| 21 | F | H | H | 3,4-dichlorobenzoyloxy- (O-C(O)-C₆H₃Cl₂) | (300 MHz, D₂O, TMSP) 2.40-2.45(m, 2 H) 2.71-2.77(m, 2 H) 5.28-5.36(m, 1 H) 7.68(d, J=8.5 Hz, 1 H) 7.89(d, J=8.5 Hz, 1 H) 8.16(s, 1 H) | ESI (Nega), 390 (M − H)⁻ | $[\alpha]_D^{28}$ +9.2 (C = 0.23 MeOH) | >270 | 9 |
| 22 | F | Et | Et | (thiophen-2-ylmethyl)thio- (S-CH₂-C₄H₃S) | (200 MHz, CDCl₃, TMS) 1.30(t, J=7.5 Hz, 3 H) 1.35(t, J=7.0 Hz, 3 H) 2.04-2.45(m, 4 H) 2.87-3.03(m, 1 H) 3.93(d, J=14.5 Hz, 1 H) 4.14(d, J=14.5 Hz, 1 H) 4.14-4.39(m, 4 H) 6.86-6.95(m, 2 H) 7.19(dd, J=4.8, 1.8 Hz, 1 H) | ESI (Pos), 410 (M + Na)⁺ | $[\alpha]_D^{22}$ +80.88 (C = 0.61 CHCl₃) | oil | 2 |

TABLE 1-continued

The structure and property data of the compounds obtained in the Examples

[Structure: cyclopentane with X, H, COOR¹, H, COOR², NH₂, Y substituents]

| Compound No. | X | R¹ | R² | Y | NMR | MS | Specific rotatory power | m.p. (° C.) | Example |
|---|---|---|---|---|---|---|---|---|---|
| 23 | F | Et | Et | S-CH₂-(2-Ph-phenyl) | (200 MHz, CDCl₃, TMS) 1.30(t, J=7.0 Hz, 3 H) 1.31(t, J=7.0 Hz, 3 H) 2.00-2.36(m, 4 H) 2.68-2.84(m, 1 H) 3.80(s, 2 H) 4.14-4.36(m, 4 H) 7.18-7.51(m, 9 H) | ESI (Pos), 480 (M + Na)⁺ | $[\alpha]_D^{22}$ +46.6 (C = 0.32 CHCl₃) | oil | 2 |
| 24 | F | Et | Et | S-CH₂-(4-OMe-phenyl) | (200 MHz, CDCl₃, TMS) 1.30(t, J=7.5 Hz, 3 H) 1.34(t, J=7.0 Hz, 3 H) 2.03-2.14(m, 1 H) 2.21-2.40(m, 3 H) 2.77-2.95(m, 1 H) 3.72-3.83(m, 5 H) 4.16-4.39(m, 4 H) 6.79-6.87(m, 2 H) 7.17-7.25(m, 2 H) | ESI (Pos), 434 (M + Na)⁺ | $[\alpha]_D^{24}$ +71.1 (C = 0.18 CHCl₃) | oil | 2 |
| 25 | F | Et | Et | S-CH₂-(4-F-phenyl) | (200 MHz, CDCl₃, TMS) 1.22-1.44(m, 6 H) 2.02-2.19(m, 1 H) 2.20-2.43(m, 3 H) 2.79-2.98(m, 1 H) 3.69-3.93(m, 2 H) 4.14-4.42(m, 4 H) 6.93-7.09(m, 2 H) 7.20-7.37(m, 2 H) | ESI (Pos), 422 (M + Na)⁺ | $[\alpha]_D^{28}$ +59.3 (C = 0.44 CHCl₃) | oil | 2 |
| 26 | F | Et | Et | S-CH₂-(4-tBu-phenyl) | (200 MHz, CDCl₃, TMS) 1.20-1.42(m, 15 H) 2.03-2.15(m, 1 H) 2.20-2.43(m, 3 H) 2.82-2.96(m, 1 H) 3.73(d, J=13.2 Hz, 1 H) 3.82(d, J=13.2 Hz, 1 H) 4.15-4.41(m, 4 H) 7.15-7.37(m, 4 H) | ESI (Pos), 460 (M + Na)⁺ | $[\alpha]_D^{30}$ +46.3 (C = 0.50 CHCl₃) | oil | 2 |
| 27 | F | Et | Et | S-CH₂-(3-CF₃-phenyl) | (200 MHz, CDCl₃, TMS) 1.19-1.42(m, 6 H) 2.02-2.43(m, 4 H) 2.81-2.95(m, 1 H) 3.83(d, J=13.2 Hz, 1 H) 3.96(d, J=13.2 Hz, 1 H) 4.07-4.41(m, 4 H) 7.33-7.65(m, 4 H) | ESI (Pos), 450 (M + H)⁺ | $[\alpha]_D^{25}$ +77.3 (C = 0.27 CHCl₃) | oil | 2 |
| 28 | F | Et | Et | S-CH₂-(1-Br-naphth-2-yl) | (200 MHz, CDCl₃, TMS) 1.30(t, J=7.0 Hz, 3 H) 1.34(t, J=7.0 Hz, 3 H) 2.03-2.14(m, 1 H) 2.21-2.44(m, 3 H) 3.01-3.15(m, 1 H) 4.05-4.40(m, 6 H) 7.45-7.64(m, 3 H) 7.78(t, J=8.1 Hz, 2 H) 8.30(d, J=8.3 Hz, 1 H) | ESI (Pos), 532 (M + Na)⁺ | $[\alpha]_D^{28}$ +101.7 (C = 0.32 CHCl₃) | oil | 2 |

TABLE 1-continued

The structure and property data of the compounds obtained in the Examples

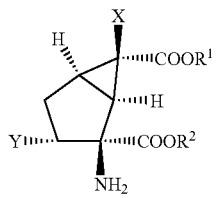

| Compound No. | X | R¹ | R² | Y | NMR | MS | Specific rotatory power | m.p. (° C.) | Example |
|---|---|---|---|---|---|---|---|---|---|
| 29 | H | Et | Bn | ![S-CH2-C6H3(3,4-Cl2)] | (200 MHz, CDCl$_3$, TMS) 1.24(t, J=7.3 Hz, 3 H) 1.77(dd, J=2.3, 2.3 Hz, 1 H) 1.80-2.17(m, 4 H) 2.46-2.55(m, 1 H) 3.65(d, J=13.6 Hz, 1 H) 3.82(d, J=13.6 Hz, 1 H) 4.09(q, J=7.3 Hz, 2 H) 5.23(s, 2 H) 7.11-7.16(m, 1 H) 7.33-7.44(m, 7 H) | ESI (Pos), 516 (M + Na)⁺ | $[\alpha]_D^{28}$ +86.35 (C = 0.23 CHCl$_3$) | oil | 2 |
| 30 | F | Et | Et | ![S-CH2-C6H3(3,4-Cl2)] | (300 MHz, CDCl$_3$, TMS) 1.31(t, J=7.2 Hz, 3 H) 1.35(t, J=7.2 Hz, 3 H) 2.08-2.15(m, 1 H) 2.24-2.40(m, 3 H) 2.86-2.93(m, 1 H) 3.73(d, J=13.4 Hz, 1 H) 3.88(d, J=13.4 Hz, 1 H) 4.21-4.37(m, 4 H) 7.15(dd, J=8.2, 2.2 Hz, 1 H) 7.36(d, J=8.2 Hz, 1 H) 7.42(d, J=2.2 Hz, 1 H) | ESI (Pos), 472 (M + Na)⁺ | $[\alpha]_D^{26}$ +94.4 (C = 0.25 CHCl$_3$) | oil | 2 |
| 31 | F | Et | Et | ![S(=O)-CH2-C6H3(3,4-Cl2)] | (200 MHz, CDCl$_3$, TMS) 1.34(t, J=7.0 Hz, 3 H) 1.35(t, J=7.0 Hz, 3 H) 2.30-2.43(m, 3 H) 2.78-3.12(m, 2 H) 3.80(d, J=13.2 Hz, 1 H) 4.19-4.36(m, 5 H) 7.17(dd, J=8.4, 2.2 Hz, 1 H) 7.44(d, J=8.4 Hz, 1 H) 7.44(d, J=2.2 Hz, 1 H) | ESI (Pos), 488 (M + Na)⁺ | $[\alpha]_D^{29}$ +59.1 (C = 0.32 CHCl$_3$) | oil | 3 |
| 32 | F | Et | Et | ![S(=O)2-CH2-C6H3(3,4-Cl2)] | (200 MHz, CDCl$_3$, TMS) 1.34(t, J=7.0 Hz, 3 H) 1.36(t, J=7.0 Hz, 3 H) 2.28-2.42(m, 3 H) 2.83-3.01(m, 1 H) 3.41-3.53(m, 1 H) 4.23-4.37(m, 6 H) 7.28(dd, J=8.4, 1.8 Hz, 1 H) 7.46(d, J=8.4 Hz, 1 H) 7.55(d, J=1.8 Hz, 1 H) | ESI (Pos), 482 (M + H)⁺ | $[\alpha]_D^{29}$ +24.0 (C = 0.86 CHCl$_3$) | oil | 4 |
| 33 | F | Et | Et | ![S-C6H3(3,4-Cl2)] | (200 MHz, CDCl$_3$, TMS) 1.31(t, J=7.5 Hz, 3 H) 1.39(t, J=7.3 Hz, 3 H) 2.13-2.35(m, 2 H) 2.43-2.74(m, 2 H) 3.26-3.41(m, 1 H) 4.18-4.46(m, 4 H) 7.26(s, 1 H) 7.32(d, J=1.3 Hz, 1 H) 7.60-7.61(m, 1 H) | ESI (Pos), 458 (M + Na)⁺ | $[\alpha]_D^{25}$ +71.2 (C = 0.28 CHCl$_3$) | oil | 2 |

TABLE 1-continued

The structure and property data of the compounds obtained in the Examples

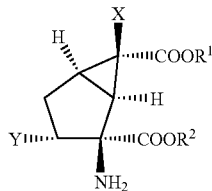

| Compound No. | X | R¹ | R² | Y | NMR | MS | Specific rotatory power | m.p. (° C.) | Example |
|---|---|---|---|---|---|---|---|---|---|
| 34 | F | Et | Et | (2,6-difluoro-3-chlorobenzyl)thio | (200 MHz, CDCl₃, TMS) 1.31(t, J=7.0 Hz, 3 H) 1.34(t, J=7.0 Hz, 3 H) 2.06-2.17(m, 1 H) 2.23-2.53(m, 3 H) 2.96-3.12(m, 1 H) 3.83(d, J=13.2 Hz, 1 H) 3.98(d, J=13.2 Hz, 1 H) 4.11-4.41(m, 4 H) 6.77-6.93(m, 1 H) 7.19-7.34(m, 1 H) | ESI (Pos), 474 (M + Na)⁺ | $[\alpha]_D^{22}$ +81.8 (C = 0.30 CHCl₃) | oil | 2 |
| 35 | F | Et | Et | SPr | (200 MHz, CDCl₃, TMS) 0.89(t, J=6.8 Hz, 3 H) 1.19-1.61(m, 10 H) 2.06-2.69(m, 6 H) 2.83-3.03(m, 1 H) 4.14-4.40(m, 4 H) | ESI (Pos), 348 (M + H)⁺ | $[\alpha]_D^{25}$ +30.5 (C = 0.24 CHCl₃) | oil | 2 |
| 36 | F | Et | Et | (1-phenylethyl)thio | (200 MHz, CDCl₃, TMS) 1.20-1.40(m, 6 H) 1.49 (d, J=7.0 Hz, 6/5 H) 1.57(d, J=7.0 Hz, 9/5 H) 1.92-2.25(m, 3 H) 2.40-2.78(m, 2 H) 4.07-4.39(m, 5 H) 7.14-7.38(m, 5 H) | ESI (Pos), 418 (M + H)⁺ | — | oil | 2 |
| 37 | F | Et | Et | bis(4-fluorophenyl)methylthio | (200 MHz, CDCl₃, TMS) 1.29(t, J=7.0 Hz, 3 H) 1.33(t, J=7.0 Hz, 3 H) 2.00-2.13(m, 1 H) 2.19-2.36(m, 3 H) 2.68-2.81(m, 1 H) 4.14-4.40(m, 4 H) 5.51(s, 1 H) 6.90-7.08 (m, 4 H) 7.21-7.31(m, 2 H) 7.36-7.48(m, 2 H) | ESI (Pos), 516 (M + H)⁺ | $[\alpha]_D^{28}$ +41.2 (C = 0.31 CHCl₃) | oil | 2 |
| 38 | F | Et | Et | (3,4-dichlorobenzyl)amino | (200 MHz, CDCl₃, TMS) 1.31(t, J=7.0 Hz, 3 H) 1.34(t, J=6.2 Hz, 3 H) 2.03-2.28(m, 3 H) 2.35-2.51(m, 1 H) 2.94-3.08(m, 1 H) 3.77(s, 2 H) 4.16-4.40(m, 4 H) 7.12(d, J=7.9 Hz, 1 H) 7.35(d, J=7.9 Hz, 1 H) 7.40(s, 1 H) | ESI (Pos), 433 (M + H)⁺ | $[\alpha]_D^{24}$ −8.4° (C = 0.56 CHCl₃) | oil | 6 |
| 39 | F | Et | Et | N-methyl-(3,4-dichlorobenzyl)amino | (300 MHz, CDCl₃, TMS) 1.33(t, J=7.0 Hz, 3 H) 1.35(t, J=7.0 Hz, 3 H) 2.06(s, 3 H) 2.03-2.21(m, 1 H) 2.23-2.60(m, 3 H) 2.68-2.84(m, 1 H) 3.22(d, J=14.1 Hz, 1 H) 3.97(d, J=14.1 Hz, 1 H) 4.18-4.32(m, 4 H) 7.07(dd, J=8.1, 2.0 Hz, 1 H) 7.30-7.39(m, 2 H) | ESI (Pos), 447 (M + H)⁺ | $[\alpha]_D^{23}$ −24.9° (C = 0.84 CHCl₃) | oil | 7 |

TABLE 1-continued

The structure and property data of the compounds obtained in the Examples

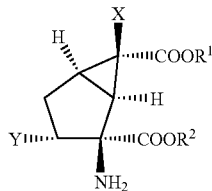

| Compound No. | X | R¹ | R² | Y | NMR | MS | Specific rotatory power | m.p. (° C.) | Example |
|---|---|---|---|---|---|---|---|---|---|
| 40 | F | Et | Et | ![3,4-dichlorobenzamide] | (200 MHz, CDCl₃, TMS) 1.30(t, J=6.8 Hz, 3 H) 1.33(t, J=7.0 Hz, 3 H) 2.09-2.43(m, 3 H) 2.53-2.38(m, 1 H) 4.19-4.38(m, 4 H) 4.52-4.71(m, 1 H) 7.48-7.55(m, 2 H) 7.75-7.84(m, 1 H) | ESI (Pos), 469 (M + Na)⁺ | $[\alpha]_D^{27}$ +8.3 (C = 0.93 CHCl₃) | oil | 8 |
| 41 | F | Et | Bn | ![3,4-dichlorobenzoate] | (200 MHz, CDCl₃, TMS) 1.33(t, J=7.3 Hz, 3 H) 2.25-2.80(m, 4 H) 4.28(q, J=7.3 Hz, 2 H) 5.05-5.13(m, 1 H) 5.16(d, J=12.3 Hz, 1 H) 5.31(d, J=12.3 Hz, 1 H) 7.24-7.36(m, 5 H) 7.44(d, J=8.4 Hz, 1 H) 7.57(dd, J=8.4, 2.20 Hz, 1 H) 7.90(d, J=2.2 Hz, 1 H) | ESI (Pos), 532 (M + Na)⁺ | $[\alpha]_D^{22}$ +31.8 (C = 0.547 CHCl₃) | oil | 9 |
| 42 | F | H | Et | ![3,4-dichlorobenzylsulfanyl] | (300 MHz, CD₃OD, TMS) 1.36(t, J=7.2 Hz, 3 H) 2.19-2.48(m, 4 H) 2.17-3.31(m, 3 H) 4.28-4.45(m, 2 H) 7.27(d, J=8.3 Hz, 1 H) 7.47(d, J=8.3 Hz, 1 H) 7.52(s, 1 H) | ESI (Nega) 420 (M − H)⁻ | | | 11 |
| 43 | F | i-Bu | H | ![3,4-dichlorobenzylsulfanyl] | (300 MHz, CD₃OD, TMS) 0.94(d, J=6.7 Hz, 6 H) 1.86-1.99(m, 1 H) 2.23-2.62(m, 4 H) 2.99-3.08(m, 1 H) 3.76(d, J=13.0 Hz, 1 H) 3.81(d, J=13.0 Hz, 1 H) 3.96(d, J=6.7 Hz, 2 H) 7.27(dd, J=8.4, 1.9 Hz, 1 H) 7.45(d, J=8.4 Hz, 1 H) 7.52(d, J=2.0 Hz, 1 H) | ESI (Pos), 472 (M + Na)⁺ | | | 10 |
| 44 | F | Bn | H | ![3,4-dichlorobenzylsulfanyl] | (300 MHz, CD₃OD, TMS) 2.19-2.43(3 H, m), 2.47-2.63(1 H, m), 2.96-3.12(1 H, m), 3.75(1 H, d, J=13.2 Hz), 3.81(1 H, d, J=13.2 Hz), 5.22(2 H, s), 7.23-7.54(8 H, m) | ESI (Nega) 482 (M − H)⁻ | | | 10 |

The compounds in the table above are as follows:
Compound No. 1: (1R,2S,3R,5R,6R)-2-amino-3-(thiophene-2-ylmethylsulfanyl)-6-fluorobicyclo[3.1.0]hexane-2,6-dicarboxylic acid;
Compound No. 2: (1R,2S,3R,5R,6R)-2-amino-3-(2-phenylbenzylsulfanyl)-6-fluorobicyclo[3.1.0]hexane-2,6-dicarboxylic acid;
Compound No. 3: (1R,2S,3R,5R,6R)-2-amino-3-(4-methoxybenzylsulfanyl)-6-fluorobicyclo[3.1.0]hexane-2,6-dicarboxylic acid;
Compound No. 4: (1R,2S,3R,5R,6R)-2-amino-3-(4-fluorobenzylsulfanyl)-6-fluorobicyclo[3.1.0]hexane-2,6-dicarboxylic acid;

Compound No. 5: (1R,2S,3R,5R,6R)-2-amino-3-(4-t-butyl-benzylsulfanyl)-6-fluorobicyclo[3.1.0]hexane-2,6-dicarboxylic acid;

Compound No. 6: (1R,2S,3R,5R,6R)-2-amino-3-(3-trifluoromethylbenzylsulfanyl)-6-fluorobicyclo[3.1.0]hexane-2,6-dicarboxylic acid;

Compound No. 7: (1R,2S,3R,5R,6R)-2-amino-3-(1-bromo-naphthalene-2-ylmethylsulfanyl)-6-fluorobicyclo[3.1.0]hexane-2,6-dicarboxylic acid;

Compound No. 8: (1R,2S,3R,5R,6R)-2-amino-3-(3,4-dichlorobenzylsulfanyl)-bicyclo[3.1.0]hexane-2,6-dicarboxylic acid;

Compound No. 9: (1R,2S,3R,5R,6R)-2-amino-3-(3,4-dichlorobenzylsulfanyl)-6-fluorobicyclo[3.1.0]hexane-2,6-dicarboxylic acid;

Compound No. 10: (1R,2S,3R,5R,6R)-2-amino-3-(3,4-dichlorobenzylsulfinyl)-6-fluorobicyclo[3.1.0]hexane-2,6-dicarboxylic acid;

Compound No. 11: (1R,2S,3R,5R,6R)-2-amino-3-(3,4-dichlorobenzylsulfonyl)-6-fluorobicyclo[3.1.0]hexane-2,6-dicarboxylic acid;

Compound No. 12: (1R,2S,3R,5R,6R)-2-amino-3-(3,4-dichlorophenylsulfanyl)-6-fluorobicyclo[3.1.0]hexane-2,6-dicarboxylic acid;

Compound No. 13: (1R,2S,3R,5R,6R)-2-amino-3-(3-chloro-2,6-difluorobenzylsulfanyl)-6-fluorobicyclo[3.1.0]hexane-2,6-dicarboxylic acid;

Compound No. 14: (1R,2S,3R,5R,6R)-2-amino-3-(propylsulfanyl)-6-fluorobicyclo[3.1.0]hexane-2,6-dicarboxylic acid;

Compound No. 15: (1R,2S,3R,5R,6R)-2-amino-3-(1-phenyl-ethylsulfanyl)-6-fluorobicyclo[3.1.0]hexane-2,6-dicarboxylic acid;

Compound No. 16: (1R,2S,3R,5R,6R)-2-amino-3-[bis-(4-fluorophenyl)methylsulfanyl]-6-fluorobicyclo[3.1.0]hexane-2,6-dicarboxylic acid;

Compound No. 17: (1R,2R,3R,5R,6R)-2,3-diamino-6-fluorobicyclo[3.1.0]hexane-2,6-dicarboxylic acid;

Compound No. 18: (1R,2R,3R,5R,6R)-2-amino-3-(3,4-dichlorobenzylamino)-6-fluorobicyclo[3.1.0]hexane-2,6-dicarboxylic acid;

Compound No. 19: (1R,2R,3R,5R,6R)-2-amino-3-[N,N-(3,4-dichlorobenzyl)methylamino]-6-fluorobicyclo[3.1.0]hexane-2,6-dicarboxylic acid;

Compound No. 20: (1R,2R,3R,5R,6R)-2-amino-3-(3,4-dichlorobenzoylamino)-6-fluorobicyclo[3.1.0]hexane-2,6-dicarboxylic acid;

Compound No. 21: (1R,2R,3R,5R,6R)-2-amino-3-(3,4-dichlorobenzoyloxy)-6-fluorobicyclo[3.1.0]hexane-2,6-dicarboxylic acid;

Compound No. 22: (1R,2S,3R,5R,6R)-2-amino-3-(thiophene-2-ylmethylsulfanyl)-6-fluorobicyclo[3.1.0]hexane-2,6-dicarboxylic acid diethyl ester;

Compound No. 23: (1R,2S,3R,5R,6R)-2-amino-3-(2-phenylbenzylsulfanyl)-6-fluorobicyclo[3.1.0]hexane-2,6-dicarboxylic acid diethyl ester;

Compound No. 24: (1R,2S,3R,5R,6R)-2-amino-3-(4-methoxybenzylsulfanyl)-6-fluorobicyclo[3.1.0]hexane-2,6-dicarboxylic acid diethyl ester;

Compound No. 25: (1R,2S,3R,5R,6R)-2-amino-3-(4-fluorobenzylsulfanyl)-6-fluorobicyclo[3.1.0]hexane-2,6-dicarboxylic acid diethyl ester;

Compound No. 26: (1R,2S,3R,5R,6R)-2-amino-3-(4-t-butylbenzylsulfanyl)-6-fluorobicyclo[3.1.0]hexane-2,6-dicarboxylic acid diethyl ester;

Compound No. 27: (1R,2S,3R,5R,6R)-2-amino-3-(3-trifluoromethylbenzylsulfanyl)-6-fluorobicyclo[3.1.0]hexane-2,6-dicarboxylic acid diethyl ester;

Compound No. 28: (1R,2S,3R,5R,6R)-2-amino-3-(1-bromo-naphthalene-2-ylmethylsulfanyl)-6-fluorobicyclo[3.1.0]hexane-2,6-dicarboxylic acid diethyl ester;

Compound No. 29: (1R,2S,3R,5R,6R)-2-amino-3-(3,4-dichlorobenzylsulfanyl)-bicyclo[3.1.0]hexane-2,6-dicarboxylic acid 2-benzyl ester 6-ethyl ester;

Compound No. 30: (1R,2S,3R,5R,6R)-2-amino-3-(3,4-dichlorobenzylsulfanyl)-6-fluorobicyclo[3.1.0]hexane-2,6-dicarboxylic acid diethyl ester;

Compound No. 31: (1R,2S,3R,5R,6R)-2-amino-3-(3,4-dichlorobenzylsulfinyl)-6-fluorobicyclo[3.1.0]hexane-2,6-dicarboxylic acid diethyl ester;

Compound No. 32: (1R,2S,3R,5R,6R)-2-amino-3-(3,4-dichlorobenzylsulfonyl)-6-fluorobicyclo[3.1.0]hexane-2,6-dicarboxylic acid diethyl ester;

Compound No. 33: (1R,2S,3R,5R,6R)-2-amino-3-(3,4-dichlorophenylsulfanyl)-6-fluorobicyclo[3.1.0]hexane-2,6-dicarboxylic acid diethyl ester;

Compound No 34: (1R,2S,3R,5R,6R)-2-amino-3-(3-chloro-2,6-difluorobenzylsulfanyl)-6-fluorobicyclo[3.1.0]hexane-2,6-dicarboxylic acid diethyl ester;

Compound No. 35: (1R,2S,3R,5R,6R)-2-amino-3-(propylsulfanyl)-6-fluorobicyclo[3.1.0]hexane-2,6-dicarboxylic acid diethyl ester;

Compound No. 36: (1R,2S,3R,5R,6R)-2-amino-3-(1-phenyl-ethylsulfanyl)-6-fluorobicyclo[3.1.0]hexane-2,6-dicarboxylic acid diethyl ester;

Compound No. 37: (1R,2S,3R,5R,6R)-2-amino-3-[bis-(4-fluorophenyl) methylsulfanyl]-6-fluorobicyclo[3.1.0]hexane-2,6-dicarboxylic acid diethyl ester;

Compound No. 38: (1R,2R,3R,5R,6R)-2-amino-3-(3,4-dichlorobenzylamino)-6-fluorobicyclo[3.1.0]hexane-2,6-dicarboxylic acid diethyl ester;

Compound No. 39: (1R,2R,3R,5R,6R)-2-amino-3-[N,N-(3,4-dichlorobenzyl)methylamino]-6-fluorobicyclo[3.1.0]hexane-2,6-dicarboxylic acid diethyl ester;

Compound No. 40: (1R,2R,3R,5R,6R)-2-amino-3-(3,4-dichlorobenzoylamino)-6-fluorobicyclo[3.1.0]hexane-2,6-dicarboxylic acid diethyl ester;

Compound No. 41: (1R,2R,3R,5R,6R)-2-amino-3-(3,4-dichlorobenzoyloxy)-6-fluorobicyclo[3.1.0]hexane-2,6-dicarboxylic acid 2-benzyl ester 6-ethyl ester;

Compound No. 42: (1R,2S,3R,5R,6R)-2-amino-3-(3,4-dichlorobenzylsulfanyl)-6-fluorobicyclo[3.1.0]hexane-2,6-dicarboxylic acid 2-ethyl ester;

Compound No. 43: (1R,2S,3R,5R,6R)-2-amino-3-(3,4-dichlorobenzylsulfanyl)-6-fluorobicyclo[3.1.0]hexane-2,6-dicarboxylic acid 6-isobutyl ester; and Compound No. 44: (1R,2S,3R,5R,6R)-2-amino-3-(3,4-dichlorobenzylsulfanyl)-6-fluorobicyclo[3.1.0]hexane-2,6-dicarboxylic acid 6-benzyl ester.

Pharmacological Test 1

Effects (or Antagonistic Action) of the Test Compound the on cAMP Accumulation in CHO Cells Modified to Stably Express Metabotropic Glutamate Receptor mGluR2

CHO cells modified to stably express metabotropic glutamate receptor mGluR2 were seeded in a 96-well plate $1.26 \times 10^4$ cells/well/0.32 cm$^2$/150 µL using Dulbecco's modified Eagle medium containing 10% dialyzed fetal bovine serum [1% proline, 50 units/mL penicillin, 50 µg/ml streptomycin, 2 mM L-glutamine (added before use)], and were cultured for 2 days at 37° C., under 5% $CO_2$ The medium was then exchanged with a L-glutamine free medium, the supernatant was removed by suction 4 hours later, and the late was washed with 150 μL of PBS(+)-IBMX (10 mM PBS(-), 1 mM $MgCl_2$, 1 mM $CaCl_2$, 1 mM IBMX), and after 100 μL of PBS(+)-IBMX containing the test compound at the final concentration of 0.3 mM to 100 μM was added, the cells were incubated for 20 minutes at 37° C., under 5% $CO_2$. After 2 μL of 500 μM forskolin (the final concentration 10 μM) was added, the cells were incubated for 15 minutes at 37° C. under 5% $CO_2$, and the effect of the test compound on the inhibitory action of glutamic acid to the forskolin-stimulated cAMP accumulation was examined (for the control, the test compounds were not added in the above procedure) (Tanabe et al, Neuron, 8, 169-179 (1992)). After 200 μL of ice-cooled ethanol was added to halt the reaction, all of the supernatant was collected into a separate plate, evaporated to dryness with an evaporator at room temperature, and stored at −20° C. The cAMP level of the dried up sample was determined with a cAMP EIA kit (Amersham Biosciences Corp.). The cAMP level of the control was subtracted from each of the cAMP levels these determined. The $IC_{50}$ of the test compound was determined, as the concentrations of the test compound antagonizes by 50% of the inhibitory action of 30 μM glutamic acid against the 10 μM forskolin-stimulated cAMP accumulation.

Among the compounds of the present invention represented by formula [II] those having hydrogen atom at $R^1$ and $R^2$ showed low $IC_{50}$ values, in the above pharmacological test.

Pharmacological Test 2

Effects of the Test Compound of the [$^3$H]MGS0008 Binding to Receptors in CHO Cells Modified to Stably Express Metabotropic Glutamate Receptor mGluR2

CHO cells modified to stably express metabotropic glutamate receptor mGluR2 were seeded in a T-225 flask using Dulbecco's modified Eagle medium containing 10% dialyzed fetal bovine serum [1% proline, 50 units/mL penicillin, 50 μg/ml streptomycin, 2 mM L-glutamine (added before use)], and were cultured for 2 days at 37° C., under 5% $CO_2$. In a state of confluency, the cells were washed twice with PBS(-), exfoliated with a cell scraper, centrifuged at 1000×g for 15 minutes at 4° C. and collected. The obtained pellet was stored at −80° C. The frozen pellet was dissolved before use and suspended in a 50 mM Tris-HCl buffer solution (pH 7.4). The buffer solution was homogenized with a homogenizer for 20 seconds and then centrifuged for 20 minutes at 4° C., 48,000×g. The pellet was again suspended and homogenized in the above buffer solution, and after being, incubated for 15 minutes at 37° C., and then centrifuged for 20 minutes at 4° C., 48,000×g. The obtained pellet was further washed twice by centrifugation and homogenized with a 50 mM Tris-HCl buffer (2 mM $MgCl_2$, pH 7.4), to obtain a membrane fraction. The receptor-binding assay was carried out at a membrane concentration between 50 to 200 μg/0.5 mL. The test compound and 3 nM [$^3$H]MGS0008 were added to the membrane fraction, followed by 1 hour of incubation at 25° C. The reaction was halted by filtering the mixture by suction with a Brandel cell harvester onto a Whatman GF/C filterer pre-soaked in 0.3% polyethylenimine. After the suction, the filter was washed three times with 3 mL of an ice-cooled buffer solution of 50 mM Tris-HCl (2 mM MgCl 2, pH 7.4). Then the filter thus obtain were soaked in 10 mL of Aquasol-2. After the filter was left to stand for over 6 hours, the fluorescence activity was measured with a Beckman LS6000 liquid scintillation counter. Non-specific binding was determined by similar fluorescence measurements in the presence of 10 μM LY354740, and the fluorescence value was subtracted from each of the binding level. The $IC_{50}$ of the test compound was determined as the concentration of the test compound showing a 50% inhibitory effect on the [$^3$H]MGS0008 binding.

The compounds of the present invention represented by formula [I] wherein $R^1$ and $R^2$ each represents a hydroxyl group and $R^3$ represents a hydrogen atom, therefore meaning compounds 1 to 58 described in table 1 above, showed a low $IC_{50}$ value of below 200 nM, which indicates a strong binding action on mGluR2 receptors, when measured as described in the pharmacological test of the present invention.

INDUSTRIAL APPLICABILITY

As shown above, compounds of the present invention may be used as metabotropic glutamate receptor antagonists. Therefore, the present invention makes it possible to provide a drug which is effective for the treatment and prevention of psychiatric disorders such as schizophrenia, anxiety and related ailments, depression, bipolar disorder and epilepsy; for the treatment and prevention of neurological diseases such as drug dependence, cognitive disorder, Alzheimer's disease, Huntington's chorea, Parkinson's disease, dyskinesia associated with muscular rigidity, cerebral ischaemia, cerebral failure, myelopathy and head trauma; and also for relieving spasms, pain, nausea and the like.

We claim:

1. A 2-amino-bicyclo[3.1.0]hexane-2,6-dicarboxylic acid derivative, a pharmaceutically acceptable salt thereof or a hydrate thereof, represented by formula [I]

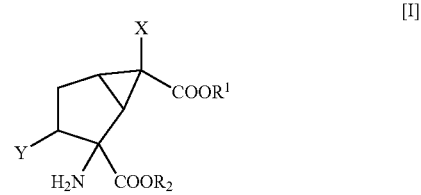

[wherein $R^1$ and $R^2$ are the same or different, and each represents a hydrogen atom, a $C_{1-10}$alkyl group, a phenyl group, a naphthyl group, a $C_{1-10}$alkyl group substituted by one or two phenyl groups, a $C_{2-10}$alkenyl group, a $C_{2-10}$alkynyl group, a hydroxyl$C_{2-10}$alkyl group, a $C_{1-10}$alkoxycarbonyl$C_{1-10}$alkyl group, an amino$C_{2-10}$alkyl group or a $C_{1-10}$alkoxy$C_{1-10}$alkyl group;

X represents a fluorine atom;

Y represents an amino group, —$SR^3$, —$S(O)_nR^7$, —$SCHR^3R^4$, —$S(O)_nCHR^3R^4$, —$NHCHR^3R^4$, —$N(CHR^3R^4)(CHR^5R^6)$, —$NHCOR^3$ or —$OCOR^7$ (wherein $R^3$, $R^4$, $R^5$ and $R^6$ are the same or different, and each represents a hydrogen atom, a $C_{1-10}$alkyl group, a phenyl group, a naphthyl group, a naphthyl group substituted by one to seven halogen atoms or a hetroaromatic group, or represents "a phenyl group substituted by one to five substituents selected from a group consisting of a halogen atom, a phenyl group, a $C_{1-10}$alkyl group, a $C_{1-10}$alkoxy group and a trifluoromethyl group";

R[7] represents a $C_{1-10}$alkyl group, a phenyl group, a naphthyl group, a naphthyl group substituted by one to seven halogen atoms or a hetroaromatic group, or represents "a phenyl group substituted by one to five substituents selected from a group consisting of a halogen atom, a phenyl group, a $C_{1-10}$alkyl group, a $C_{1-10}$alkoxy group and a trifluoromethyl group"; and n represents integer 1 or 2)].

2. A 2-amino-bicyclo[3.1.0]hexane-2,6-dicarboxylic acid derivative, a pharmaceutically acceptable salt thereof or a hydrate thereof, represented by formula [II]

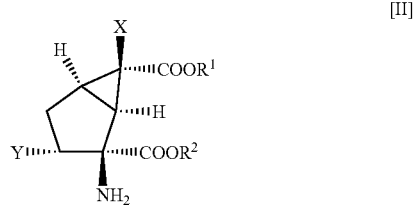

[Wherein R[1] and R[2] are the same or different, and each represents a hydrogen atom, a $C_{1-10}$alkyl group, a phenyl group, a naphthyl group, a $C_{1-10}$alkyl group substituted by one or two phenyl groups, a $C_{2-10}$alkenyl group, a $C_{2-10}$alkynyl group, a hydroxyl$C_{2-10}$alkyl group, a $C_{1-10}$alkoxycarbonyl$C_{1-10}$alkyl group, an amino$C_{2-10}$alkyl group or a $C_{1-10}$alkoxy$C_{1-10}$alkyl group;

X represents a fluorine atom;

Y represents an amino group, —SR[3], —S(O)$_n$R[7], —SCHR[3]R[4], —S(O)$_n$CHR[3]R[4], —NHCHR[3]R[4], —N(CHR[3]R[4])(CHR[5]R[6]), —NHCOR[3] or —OCOR[7] (wherein R[3], R[4], R[5] and R[6] are the same or different, and each represents a hydrogen atom, a $C_{1-10}$alkyl group, a phenyl group, a naphthyl group, a naphthyl group substituted by one to seven halogen atoms or a hetroaromatic group, or represents "a phenyl group substituted by one to five substituents selected from a group consisting of a halogen atom, a phenyl group, a $C_{1-10}$alkyl group, a $C_{1-10}$alkoxy group and a trifluoromethyl group";

R[7] represents a $C_{1-10}$alkyl group, a phenyl group, a naphthyl group, a naphthyl group substituted by one to seven halogen atoms or a hetroaromatic group or represents "a phenyl group substituted by one to five substituents selected from a group consisting of a halogen, a phenyl group, a $C_{1-10}$alkyl group, a $C_{1-10}$alkoxy group and a trifluoromethyl group"; and n represents integer 1 or 2)].

3. A 2-amino-bicyclo[3.1.0]hexane-2,6-dicarboxylic acid derivative according to claim 2, a pharmaceutically acceptable salt thereof or a hydrate thereof, represented by formula [II] wherein R[2] represents a hydrogen.

4. A 2-amino-bicyclo[3.1.0]hexane-2,6-dicarboxylic acid derivative according to claim 2, a pharmaceutically acceptable salt thereof or a hydrate thereof, represented by formula [II] wherein R[1] and R[2] each represents a hydrogen.

5. A 2-amino-bicyclo[3.1.0]hexane-2,6-dicarboxylic acid derivative according to claim 2, a pharmaceutically acceptable salt thereof or a hydrate thereof, represented by formula [II] wherein R[1] and R[2] each represents a hydrogen atom; Y represents —SR[3] (—SR[3] is the same as mentioned above).

6. A 2-amino-bicyclo[3.1.0]hexane-2,6-dicarboxylic acid derivative according to claim 2, a pharmaceutically acceptable salt thereof or a hydrate thereof, represented by formula [II] wherein R[1] and R[2] each represents a hydrogen atom; and Y represents —S(O)$_n$R[7] (—S(O)$_n$R[7] is the same as mentioned above).

7. A 2-amino-bicyclo[3.1.0]hexane-2,6-dicarboxylic acid derivative according to claim 2, a pharmaceutically acceptable salt thereof or a hydrate thereof, such a compound of formula [II] being:

(1R,2S,3R,5R,6R)-2-amino-3-(thiophene-2-ylmethylsulfanyl)-6-fluorobicyclo[3.1.0]hexane-2,6-dicarboxylic acid;

(1R,2S,3R,5R,6R)-2-amino-3-(2-phenylbenzylsulfanyl)-6-fluorobicyclo[3.1.0]hexane-2,6-dicarboxylic acid;

(1R,2S,3R,5R,6R)-2-amino-3-(4-methoxybenzylsulfanyl)-6-fluorobicyclo[3.1.0]hexane-2,6-dicarboxylic acid;

(1R,2S,3R,5R,6R)-2-amino-3-(4-fluorobenzylsulfanyl)-6-fluorobicyclo[3.1.0]hexane-2,6-dicarboxylic acid;

(1R,2S,3R,5R,6R)-2-amino-3-(4-t-butylbenzylsulfanyl)-6-fluorobicyclo[3.1.0]hexane-2,6-dicarboxylic acid;

(1R,2S,3R,5R,6R)-2-amino-3-(3-trifluoromethylbenzylsulfanyl)-6-fluorobicyclo[3.1.0]hexane-2,6-dicarboxylic acid;

(1R,2S,3R,5R,6R)-2-amino-3-(1-bromo-naphthalene-2-ylmethylsulfanyl)-6-fluorobicyclo[3.1.0]hexane-2,6-dicarboxylic acid;

(1R,2S,3R,5R,6R)-2-amino-3-(3,4-dichlorobenzylsulfanyl)-6-fluorobicyclo[3.1.0]hexane-2,6-dicarboxylic acid;

(1R,2S,3R,5R,6R)-2-amino-3-(3,4-dichlorobenzylsulfinyl)-6-fluorobicyclo[3.1.0]hexane-2,6-dicarboxylic acid;

(1R,2S,3R,5R,6R)-2-amino-3-(3,4-dichlorobenzylsulfonyl)-6-fluorobicyclo[3.1.0]hexane-2,6-dicarboxylic acid;

(1R,2S,3R,5R,6R)-2-amino-3-(3,4-dichlorophenylsulfanyl)-6-fluorobicyclo[3.1.0]hexane-2,6-dicarboxylic acid;

(1R,2S,3R,5R,6R)-2-amino-3-(3-chloro-2,6-difluorobenzylsulfanyl)-6-fluorobicyclo[3.1.0]hexane-2,6-dicarboxylic acid; (1R,2S,3R,5R,6R)-2-amino-3-(propylsulfanyl)-6-fluorobicyclo[3.1.0]hexane-2,6-dicarboxylic acid;

(1R,2S,3R,5R,6R)-2-amino-3-(1-phenyl-ethylsulfanyl)-6-fluorobicyclo[3.1.0]hexane-2,6-dicarboxylic acid;

(1R,2S,3R,5R,6R)-2-amino-3-[bis-(4-fluorophenyl)methylsulfanyl]-6-fluorobicyclo[3.1.0]hexane-2,6-dicarboxylic acid;

(1R,2R,3R,5R,6R)-2,3-diamino-6-fluorobicyclo[3.1.0]hexane-2,6-dicarboxylic acid;

(1R,2R,3R,5R,6R)-2-amino-3-(3,4-dichlorobenzylamino)-6-fluorobicyclo[3.1.0]hexane-2,6-dicarboxylic acid;

(1R,2R,3R,5R,6R)-2-amino-3-[N,N-(3,4-dichlorobenzyl)methylamino]-6-fluorobicyclo[3.1.0]hexane-2,6-dicarboxylic acid;

(1R,2R,3R,5R,6R)-2-amino-3-(3,4-dichlorobenzoylamino)-6-fluorobicyclo[3.1.0]hexane-2,6-dicarboxylic acid; or (1R,2R,3R,5R,6R)-2-amino-3-(3,4-dichlorobenzoyloxy)-6-fluorobicyclo[3.1.0]hexane-2,6-dicarboxylic acid.

8. A 2-amino-bicyclo[3.1.0]hexane-2,6-dicarboxylic acid derivative according to claim 2, a pharmaceutically acceptable salt thereof or a hydrate thereof, such a compound of formula [II] being:

(1R,2R,3R,5R,6R)-2,3-diamino-6-fluorobicyclo[3.1.0]hexane-2,6-dicarboxylic acid diethyl ester;

(1R,2S,3R,5R,6R)-2-amino-3-(thiophene-2-ylmethylsulfanyl)-6-fluorobicyclo[3.1.0]hexane-2,6-dicarboxylic acid diethyl ester;

(1R,2S,3R,5R,6R)-2-amino-3-(2-phenylbenzylsulfanyl)-6-fluorobicyclo[3.1.0]hexane-2,6-dicarboxylic acid diethyl ester;

(1R,2S,3R,5R,6R)-2-amino-3-(4-methoxybenzylsulfanyl)-6-fluorobicyclo[3.1.0]hexane-2,6-dicarboxylic acid diethyl ester;

(1R,2S,3R,5R,6R)-2-amino-3-(4-fluorobenzylsulfanyl)-6-fluorobicyclo[3.1.0]hexane-2,6-dicarboxylic acid diethyl ester;

(1R,2S,3R,5R,6R)-2-amino-3-(4-t-butylbenzylsulfanyl)-6-fluorobicyclo[3.1.0]hexane-2,6-dicarboxylic acid diethyl ester;

(1R,2S,3R,5R,6R)-2-amino-3-(3-trifuoromethylbenzylsulfanyl)-6-fluorobicyclo[3.1.0]hexane-2,6-dicarboxylic acid diethyl ester;

(1R,2S,3R,5R,6R)-2-amino-3-(1-bromo-naphthalene-2-ylmethylsulfanyl)-6-fluorobicyclo[3.1.0]hexane-2,6-dicarboxylic acid diethyl ester;

(1R,2S,3R,5R,6R)-2-amino-3-(3,4-dichlorobenzylsulfanyl)-6-fluorobicyclo[3.1.0]hexane-2,6-dicarboxylic acid diethyl ester;

(1R,2S,3R,5R,6R)-2-amino-3-(3,4-dichlorobenzylsulfinyl)-6-fluorobicyclo[3.1.0]hexane-2,6-dicarboxylic acid diethyl ester;

(1R,2S,3R,5R,6R)-2-amino-3-(3,4-dichlorobenzylsulfonyl)-6-fluorobicyclo[3.1.0]hexane-2,6-dicarboxylic acid diethyl ester;

(1R,2S,3R,5R,6R)-2-amino-3-(3,4-dichlorophenylsulfanyl)-6-fluorobicyclo[3.1.0]hexane-2,6-dicarboxylic acid diethyl ester;

(1R,2S,3R,5R,6R)-2-amino-3-(3-chloro-2,6-difluorobenzylsulfanyl)-6-fluorobicyclo[3.1.0]hexane-2,6-dicarboxylic acid diethyl ester;

(1R,2S,3R,5R,6R)-2-amino-3-(propylsulfanyl)-6-fluorobicyclo[3.1.0]hexane-2,6-dicarboxylic acid diethyl ester;

(1R,2S,3R,5R,6R)-2-amino-3-(1-phenyl-ethylsulfanyl)-6-fluorobicyclo[3.1.0]hexane-2,6-dicarboxylic acid diethyl ester;

(1R,2S,3R,5R,6R)-2-amino-3-[bis-(4-fluorophenyl)methylsulfanyl]-6-fluorobicyclo[3.1.0]hexane-2,6-dicarboxylic acid diethyl ester;

(1R,2R,3R,5R,6R)-2-amino-3-(3,4-dichlorobenzylamino)-6-fluorobicyclo[3.1.0]hexane-2,6-dicarboxylic acid diethyl ester;

(1R,2R,3R,5R,6R)-2-amino-3-[N,N-(3,4-dichlorobenzyl)methylamino]-6-fluorobicyclo[3.1.0]hexane-2,6-dicarboxylic acid diethyl ester;

(1R,2R,3R,5R,6R)-2-amino-3-(3,4-dichlorobenzoylamino)-6-fluorobicyclo[3.1.0]hexane-2,6-dicarboxylic acid diethyl ester;

(1R,2R,3R,5R,6R)-2-amino-3-(3,4-dichlorobenzoyloxy)-6-fluorobicyclo[3.1.0]hexane-2,6-dicarboxylic acid 2-benzyl ester 6-ethyl ester;

(1R,2S,3R,5R,6R)-2-amino-3-(3,4-dichlorobenzylsulfanyl)-6-fluorobicyclo[3.1.0]hexane-2,6-dicarboxylic acid 2-ethyl ester;

(1R,2S,3R,5R,6R)-2-amino-3-(3,4-dichlorobenzylsulfanyl)-6-fluorobicyclo[3.1.0]hexane-2,6-dicarboxylic acid 6-isobutyl ester; or (1R,2S,3R,5R,6R)-2-amino-3-(3,4-dichlorobenzylsulfanyl)-6-fluorobicyclo[3.1.0]hexane-2,6-dicarboxylic acid 6-benzyl ester.

9. A drug comprising the 2-amino-bicyclo[3.1.0]hexane-2,6-dicarboxylic acid derivative according to claim 1, the pharmaceutically acceptable salt thereof or the hydrate thereof as an active ingredient.

10. The drug according to claim 9 wherein the drug is a Group II metabotropic glutamate receptor antagonist.

\* \* \* \* \*